(12) United States Patent
DeMeritt

(10) Patent No.: US 12,178,440 B2
(45) Date of Patent: *Dec. 31, 2024

(54) MICRO-MACRO ENDOVASCULAR OCCLUSION DEVICE AND METHODOLOGY

(71) Applicant: John S. DeMeritt, Saddle River, NJ (US)

(72) Inventor: John S. DeMeritt, Saddle River, NJ (US)

(*) Notice: Subject to any disclaimer, the term of this patent is extended or adjusted under 35 U.S.C. 154(b) by 548 days.

This patent is subject to a terminal disclaimer.

(21) Appl. No.: 17/411,788

(22) Filed: Aug. 25, 2021

(65) Prior Publication Data

US 2021/0378680 A1 Dec. 9, 2021

Related U.S. Application Data

(63) Continuation of application No. 16/379,339, filed on Apr. 9, 2019, now Pat. No. 11,116,511, which is a continuation of application No. 16/014,201, filed on Jun. 21, 2018, now Pat. No. 10,299,799, application No. 17/411,788 is a continuation-in-part of
(Continued)

(51) Int. Cl.
*A61B 17/12* (2006.01)
*A61B 17/00* (2006.01)

(52) U.S. Cl.
CPC .... *A61B 17/12145* (2013.01); *A61B 17/0057* (2013.01); *A61B 17/12031* (2013.01); *A61B 17/12109* (2013.01); *A61B 17/12113* (2013.01); *A61B 17/12122* (2013.01); *A61B 17/1214* (2013.01); *A61B 17/1215* (2013.01); *A61B 17/12172* (2013.01); *A61B 17/12177* (2013.01); *A61B 2017/00292* (2013.01); *A61B 2017/00592* (2013.01); *A61B 2017/00632* (2013.01); *A61B 2017/00778* (2013.01); *A61B 2017/00867* (2013.01); *A61B 17/12036* (2013.01);
(Continued)

(58) Field of Classification Search
CPC ......... A61B 17/0057; A61B 17/12113; A61B 17/1215; A61B 17/12145; A61B 17/12172; A61B 17/12177; A61B 2017/00575; A61B 2017/00592; A61B 2017/00632
See application file for complete search history.

(56) References Cited

U.S. PATENT DOCUMENTS 8,361,104 B2 1/2013 Jones et al.
8,641,777 B2 2/2014 Strauss et al.
(Continued)

FOREIGN PATENT DOCUMENTS

FR 2943905 A1 10/2010

*Primary Examiner* — Robert A Lynch
(74) *Attorney, Agent, or Firm* — Neil D. Gershon

(57) ABSTRACT

A vascular plug comprises a superstructure expandable from a collapsed percutaneous insertion configuration to an expanded deployment or use configuration. The superstructure is comprised of both primary and secondary three-dimensional shapes allowing for the occlusion of a wide range of vessel sizes from small to large through a disproportionately small delivery catheter. The plug includes a shape memory element for the generation of radial force and the creation of the larger secondary three-dimensional twisting or helical superstructure as is needed for target vessel occlusion.

19 Claims, 36 Drawing Sheets

Related U.S. Application Data application No. 16/014,201, filed on Jun. 21, 2018, now Pat. No. 10,299,799.

(60) Provisional application No. 62/529,738, filed on Jul. 7, 2017.

(52) U.S. Cl.
CPC ............... *A61B 2017/1205* (2013.01); *A61B 2017/12054* (2013.01); *A61B 2017/12127* (2013.01)

(56) References Cited

U.S. PATENT DOCUMENTS

| | | | |
|---|---|---|---|
| 8,715,316 B1 | 5/2014 | Janardhan et al. | |
| 9,060,777 B1* | 6/2015 | Wallace | A61F 2/07 |
| 10,299,799 B1* | 5/2019 | DeMeritt | A61B 17/12177 |
| 11,116,511 B2* | 9/2021 | DeMeritt | A61B 17/12172 |
| 2005/0004598 A1 | 1/2005 | White | A61B 17/1215 |
| | | | 606/200 |
| 2006/0116713 A1 | 6/2006 | Sepetka et al. | |
| 2006/0212055 A1* | 9/2006 | Karabey | A61B 17/1219 |
| | | | 606/158 |
| 2012/0226304 A1 | 9/2012 | Ryan | A61B 17/12109 |
| | | | 606/200 |
| 2012/0283768 A1 | 11/2012 | Cox et al. | |
| 2013/0253572 A1 | 9/2013 | Molaei et al. | |
| 2014/0163599 A1 | 6/2014 | Wijay | |
| 2014/0277090 A1 | 9/2014 | Fercik Grant | A61B 17/12145 |
| | | | 606/200 |
| 2015/0039017 A1 | 2/2015 | Cragg et al. | |
| 2015/0039020 A1 | 2/2015 | Cragg et al. | |
| 2015/0045874 A1 | 2/2015 | McMahon | |
| 2016/0030050 A1 | 2/2016 | Franano et al. | |
| 2016/0143646 A1 | 5/2016 | Ryan et al. | |
| 2016/0206323 A1 | 7/2016 | Stephen et al. | |
| 2017/0035430 A1 | 2/2017 | Sarge et al. | |
| 2017/0035437 A1* | 2/2017 | Sarge | A61B 17/12163 |
| 2018/0014829 A1 | 1/2018 | Tal | A61B 17/12109 |
| 2018/0036012 A1 | 2/2018 | Aboytes et al. | |

\* cited by examiner

MICRO-MACRO ENDOVASCULAR OCCLUSION DEVICE AND METHODOLOGY

This application is a continuation of application Ser. No. 16/379,339, now U.S. Pat. No. 11,116,511, filed Apr. 9, 2019 as a continuation of application Ser. No. 16/014,201 filed Jun. 21, 2018, now U.S. Pat. No. 10,299,799. This application also claims the benefit of U.S. Provisional Patent Application No. 62/529,738 filed Jul. 7, 2017.

BACKGROUND OF THE INVENTION

The present disclosure generally relates to a device and methodology for occluding arterial and venous blood vessels under a variety of pathologic conditions.

Many endovascular devices exist for occluding blood flow including coils, detachable balloons, and most recently expandable mechanical occlusive devices with or without coverings impervious to blood flow. Coils can be covered with fibers or coated with material such as hydrogel to enhance clot formation. Despite these features many coils are often required to occlude blood flow increasing procedure time and potentially cost. Coils can also be unreliable with regards to their geometry and vascular space filling properties after deployment. In addition coils and or clot can easily migrate distally under high flow condition such as arteriovenous fistula in the lungs or elsewhere in the body. Blood vessels occluded by coils can reopen or recanalize as has been reported in pulmonary arteriovenous fistula. Detachable balloons can be difficult to navigate through blood vessels and can prematurely detach. Premature balloon detachment can lead to migration and occlusion of normal blood vessels resulting in complications. Balloons can deflate over time resulting in recurrence of the treated vascular pathology such as has been reported in carotico-cavernous fistula. More recently detachable uncovered and membrane covered expandable mechanical occlusive devices have been developed in an attempt to occlude blood flow more rapidly, permanently, and with more spatial precision; commonly referred to as vascular plugs. These include the uncovered detachable Amplatzer vascular plug which is made of a self-expanding Nitinol mesh, it is delivered through catheters or sheaths of varying size, inciting vessel thrombosis. This device may not immediately lead to thrombosis particularly in patients with clotting disorders, requiring more than one device. The device can be difficult to deliver and precisely deploy. In addition the device may not provide long-term occlusion, which has been reported in pulmonary arteriovenous fistula in particular. Covered devices such as the MVP microplug can provide immediate occlusion with good long-term occlusion in early studies. The MVP is the only covered plug that can be delivered through a microcatheter, particularly advantageous when navigating through tortuous anatomy and smaller vessels. The largest MVP microcatheter deliverable covered plug can only treat vessels up to 5 mm in diameter, a distinct disadvantage. Larger MVP covered plugs require delivery through 4 or 5 French catheters depending on the target vessel size; these larger catheters are often too big and rigid to easily traverse the desired vasculature. The use of these larger 4 and 5 French catheters to target the more distal vasculature can lead to technical failures, vessel spasm and vascular injury. Vessels up to 7 mm can be treated through a 4 French catheter while vessels up to 9 mm can be treated through a 5 french catheter with the MVP device. The device may not be ideal for high flow situations with possible migration considering it's small footprint and vessel anchoring capabilities. Precise measuring or sizing relative to the target vessel is important. The relatively small length rigid nitinol frame is best suited for straight vessel segments or horizontal deployment zones.

It would be desirable to occlude larger vessels than 5 mm through a microcatheter with a covered plug, not currently possible with available devices such as the MVP. Microcatheters are usually manufactured with two different size internal diameters, namely 0.021 inch (standard) and 0.027 inch (high-flow). Larger 4 French and 5 French diagnostic catheters typically have internal diameters of 0.040 inch and 0.046 inch respectively. 5 French diagnostic angiographic catheters are typically used to catheterize the origins or proximal aspects of the major branch vessels arising in the neck, chest, abdomen, pelvis and lower extremities; and can accommodate both standard and high flow microcatheters. These larger 5 French diagnostic catheters are often difficult to advance more distally into the primary or secondary aortic branch vessels such as the hepatic artery, splenic artery, renal artery, internal carotid artery and hypogastric artery to name a few. It would be clinically advantageous to be able to occlude vessels larger than 5 mm with a microcatheter deliverable covered vascular plug, advanced through a 5 French angiographic catheter. The target vessels for occlusion are often larger than 5 mm, precluding the use of a microcatheter for vascular plug delivery by current means and methods. In addition, microcatheters are advantageous for traversing tortuous anatomy, often difficult or impossible with larger 5 French catheters. Venous embolization often entails occluding even larger caliber vessels than arteries, often necessitating larger guiding catheters or sheaths for device delivery, such as the uncovered Amplatzer plugs.

It is preferable on many occasions to occlude a blood vessel on both the upstream and downstream sides relative to a given arterial or venous vascular pathology, i.e. to mechanically occlude a vascular segment. This can be difficult and or cumbersome to achieve with current available devices. For example it can be desirable to occlude a fusiform aneurysm or abnormal ballooning of a blood vessel on both sides since the aneurysm might still fill or stay open after just upstream occlusion of the artery. A fusiform aneurysm is spindle or football shaped; it bulges or balloons out on all sides of the blood vessel. Flow can reverse through collateral filling in the downstream portion of the artery relative to the fusiform aneurysm, after just upstream occlusion by a vascular plug, thereby maintaining patency of the aneurysm. Initial occlusion of the downstream portion of the vessel relative to the fusiform aneurysm can result in increased flow and pressure in the aneurysm resulting in rupture. It is generally safer under these circumstances to occlude distally only under the conditions of proximal flow and pressure control (flow arrest) to prevent possible vessel rupture.

It is often desirable to primarily occlude saccular intracranial or peripheral saccular aneurysms while simultaneously sparing the parent vessel from which it arises. A saccular aneurysm is a blind ending vascular outpouching or sac, which arises only from one side of the blood vessel. The occlusion or closing of a saccular aneurysm is often accomplished by placing multiple coils of varying shapes and sizes directly within the aneurysm sac. Although effective this process can be cumbersome when using current methods, particularly for larger aneurysms, requiring multiple coils to fill the aneurysm sac. In addition the coils can compact overtime with aneurysm recurrence, typically occurring at the aneurysm neck or site of connection with the parent vessel. Coils can also prolapse into the parent vessel if the aneurysm neck is wide. It has been shown that disruption of flow within the blind ending aneurysm sac leading to thrombosis can be achieved even with uncovered porous or mesh like intra-aneurysmal space filling devices, often called flow disruptors. It would desirable to have an intra-aneurysmal space filling occlusive device that could approximate the spherical or ellipsoid shape typical of a saccular aneurysm with either a single or limited number of devices in order to more rapidly, effectively, and perhaps more permanently occlude the aneurysm sac.

OBJECTS OF THE INVENTION

It is an object of the present invention to provide an improved vascular occlusion device and/or an associated surgical method, which addresses the afore-mentioned problems.

It is a more specific object of the present invention to provide an improved vascular occlusion device and/or an associated surgical method which enables the deployment through a microcatheter of a vascular plug which can assume a much larger shape and thereby occlude small, medium, or large vessels with the same device delivered via a microcatheter. This is not possible with current devices.

It is an even more specific object of the present invention to provide an improved vascular occlusion device and/or an associated surgical method, which allows for the occlusion of vessels both smaller and larger than 5 mm, the current upper limit for a microcatheter deliverable plug. Preferably, the same design could be used for 4 and 5 French deliverable devices to occlude even larger arteries, veins, aneurysms, or varicoceles.

Another specific object of the present invention to provide an improved vascular occlusion device and/or an associated surgical method wherein an occlusive vascular plug allows for a very large space filling capacity in proportion to the delivery catheter diameter, thereby facilitating large vessel or large aneurysm occlusion, currently not possible with current devices.

Yet another object of the present invention is to provide an improved vascular occlusion device and/or an associated surgical method wherein vessel thrombosis occurs gradually after a period of time, thereby preventing device migration in high flow situations, enabling the operator time to create a stable intravascular construct.

Another more specific object of the present invention is to provide an improved vascular occlusion device and/or an associated surgical method which enables the deployment or installation one or more vascular occlusion devices or plugs in a patient's vascular system completely across a given segmental vascular pathology such as a fusiform aneurysm, simultaneously occluding both down stream and upstream relative to a given vascular pathology.

Another more specific object of the present invention is to provide an improved vascular occlusion device and/or an associated surgical method which allows for primary treatment of saccular intracranial or peripheral aneurysms.

Another more specific object of the present invention is to provide an improved vascular occlusion device and/or an associated surgical method wherein the cumulative radial force exerted by the primary and secondary device structure is improved over the current available microcatheter deliverable vascular plug.

Another more specific object of the present invention is to provide an improved vascular occlusion device and/or an associated surgical method wherein the device is easily deployed and configured in curved vascular segments.

Another more specific object of the present invention is to provide a space filling device and/or an associated surgical method for occluding pathologic nonvascular spaces related to the bowel, bile ducts, or ureters, for example.

A further object of the present invention is to provide an improved vascular occlusion device and/or an associated minimally invasive surgical method.

These and other objects of the present invention will be apparent from the drawings and descriptions hereof. Although every object of the invention is considered to be attained by at least one embodiment of the invention, there is not necessarily any single embodiment that achieves all of the objects of the invention.

SUMMARY OF THE INVENTION

The present invention is directed collapsible tubular structure, which is self-expanding to assume a tubular form and further self-configuring to assume an even larger secondary spiraling superstructure. This occlusive medical device is designed to solve the problem of occluding large arteries and veins via a microcatheter. A coiled or spiraling wire shape memory element is incorporated within an otherwise flexible and conformable tubular plug body to form the plug body into a large space-filling secondary helical or twisting shape. Depending on the target vessel size, two successively placed parallel or interlocking devices might be required for complete vascular occlusion, forming a double helix configuration, for example. The same device could be used to occlude even bigger vessels utilizing diameter 4 and 5 French catheter deliverable vascular plugs, at the expense of less navigability and a larger external delivery catheter diameter. The secondary plug configuration is in essence a hybrid plug-coil design, which results in a spiraling three-dimensional tubular helical superstructure.

The tubular structure or plug body is typically provided with an outer covering or membrane that may be impermeable or partially permeable. Partially permeable membranes provide gradual occlusion as perforations in the membrane are blocked with thrombus and close at a rate depending on pore size.

In another version of a self-expanding occlusive medical device pursuant to the present invention, the plug body is uncovered, optionally coated with various thrombogenic materials such as small fibers or hydrogel, to engender vessel thrombosis by the three-dimensional spiraling superstructure or scaffolding after deployment.

The tubular structure is made of shape memory wiring in a self-expanding network where wires selectively slide relative to one another. Such cages or lattice structures, self-expanding or mechanically expandable exemplarily via balloons, are well-known in the vascular arts.

A vascular plug or medical occlusion device in accordance with the present invention comprises a superstructure expandable from a collapsed insertion configuration to an expanded deployment or use configuration. The insertion configuration is sufficiently small to enable percutaneous introduction into a patient's vascular system. The expanded deployment or use configuration is sufficiently large to extend across a target blood vessel and engage an endothelial surface of such blood vessel. The superstructure is advanced through a microcatheter or larger catheter attached to a deployment wire. The occlusive device has primary and secondary shapes. The primary shape is a tubular covered or uncovered plug with a lattice-work outer wall made of strands or wires of a spring-loaded or shape memory material such as nitinol or other metal alloys. The secondary shape is a three-dimensional spiraling or helical configuration of the primary tubular shape and is created by an additional internal shape memory element or wire incorporated within an otherwise flexible and conformable plug body. The additional shape memory element of wire has a coiled base (unstressed) configuration and exerts sufficiently strong shape-memory force to twist the tubular structure or plug into the spiraling or helical configuration. The tubular structure or plug may be attached to the end of a manipulation tether or wire and released therefrom by a mechanical detachment mechanism or other means after formation of the primary shape and optionally the secondary shape, depending on the target vessel size.

A vascular occlusion device in accordance with the present invention may be covered with an impervious membrane, uncovered, or alternatively coated with various thrombogenic materials such as small fibers or hydrogel to engender thrombosis by the three-dimensional spiraling superstructure or scaffolding after deployment. The porosity of an uncovered plug wall or body may be selected so as to promote thrombosis; changing the weave pattern or design of the stent body may be done to lower the porosity of the plug wall, and hence increase its thrombogenicity. A low porosity device has minimal flow through it; a zero porosity device is impervious to flow. A plug wall with the lowest porosity possible while still maintaining the desired primary and secondary plug properties and shapes is ideal. An uncovered low porosity plug can have an overall lower profile relative to even a thinly covered plug.

The porosity of the wall of a vascular plug or medical occlusion device in accordance with the invention can be tailored to different clinical and pathologic conditions. A very low porosity plug is more thrombogenic than a higher porosity plug, while a higher porosity plug would be less susceptible than a low porosity plug to migration under the conditions of high flow, enabling the operator to create an initial stable construct or scaffolding with one or more uncovered higher porosity plugs, with subsequent placement of one or more covered or very low porosity devices in order to complete vessel occlusion.

The intraplug porosity of a given occlusion device or plug may also be varied from an upstream portion of the plug to a downstream portion. The upstream portion of the plug could have a low porosity to promote stasis and thrombosis, while the downstream portion could have a higher porosity to allow for blood flow into and out of a lumen of the plug, facilitating device repositioning or removal prior to final plug deployment. A partially porous covering plug membrane could be provided on the downstream end of a plug to achieve a similar result: transient limited flow through the plug body to reduce the chances of migration with subsequent thrombosis.

An uncovered plug may be coated with an expanding hydrogel material, which would be activated after coming in contact with blood after deployment, thereby lowering the porosity of the plug wall over time, engendering both intraplug and target vessel thrombosis. A hydrogel-coated plug might be useful in a high flow setting allowing time for deployment of two stable interlocking plug devices prior to the assembled construct becoming impervious to flow. The two plug or occlusion devices may be inserted either simultaneously via two delivery catheters traversing a single large guiding catheter, or in succession via one catheter, decreasing the chances of device migration. In other words the use of a hydrogel coating would allow for the creation of an occlusive plug that would decrease its porosity over time after initial deployment, which could be exploited to more easily treat high flow pathologic conditions.

Mechanical plug compaction after initial deployment could be used to decrease the porosity of an uncovered plug, by compressing the weave pattern in the plug wall, thereby decreasing the plug wall porosity.

The present invention provides a membrane-covered or uncovered vascular occlusion device that is deliverable to a target site via a micro-catheter or even a 4 or 5 French catheter deliverable and is capable of occluding or filling a larger vascular volume than is currently possible. An occlusion device in accordance with the present invention is of great clinical benefit for treating various vascular pathologies including but not limited to bleeding vessels, arterial aneurysms, venous aneurysms, and varices. An even larger space filling capacity is achievable by assembling in situ a device by intertwining or interlocking two or more successively deployed intravascular subunits. Thus, a first deployed occlusion device in accordance with the present invention may assume on deployment in a large vessel or space a spiraling tubular configuration with a central passageway which is plugged by the insertion and expansion therein of a second occlusion device preferably of the same or similar spiraling tubular deployment configuration. Such a variation of the present invention is useful for occluding large blood vessels, aneurysms, or pathologic vascular spaces such as the left atrial appendage in the setting of atrial fibrillation over current methods.

The present invention therefore contemplates an in situ formation of an occlusion assembly from a plurality of separate occlusion devices or plugs. More particularly, the method entails an assembling or intertwining two or more successively deployed devices or intravascular subunits. At least a first of the deployed devices or intravascular subunits has a spiraling tubular configuration upon expansion from a collapsed insertion configuration. This first deployed device or intravascular subunit expands to engage an endothelium of a target vessel or organ. Where the expanded first deployed device or intravascular subunit has a channel or passageway, at least one second deployed device or intravascular subunit is inserted, at least partially collapsed, in the channel or passageway and expanded to fill and plug the channel or passageway. The second deployed device or intravascular subunit may become interlocked with the first deployed device or intravascular subunit, possibly becoming seated in a spiraling groove or inter-turn gap or cleavage of the first deployed device or intravascular subunit. On occasion it may be beneficial or necessary to utilize a third deployed device or intravascular subunit, which is inserted into a cavity or recess that may exist in the assembly of the first and second deployed devices or intravascular subunits.

For treating segmental vascular pathology, particularly long segment vascular disease such as an elongated fusiform aneurysm, the present invention contemplates an elongated microcatheter-deliverable vascular plug or occlusion device that is variously expandable to extend completely across segmental vascular pathology in both small and large vessels. This methodology both nearly simultaneously occludes the fusiform aneurysm along its downstream and upstream portions, minimizing the risk of altered hemodynamics and aneurysm rupture during plug deployment, but also prevents downstream aneurysm retrograde reconstitution secondary to flow reversal. A modified solution to the problem of more safely treating segmental vascular pathology, particularly useful for long segment vascular disease such as an elongated fusiform aneurysm, is the placement of successive devices in a strategic manner (endovascular trapping), two such devices being deployed through the same catheter to simultaneously occlude both proximally and distally to the lesion (e.g., a fusiform aneurysm). A first proximal occlusive device is placed to reduce inflow to the lesion, and has a channel or aperture (for instance, a doughnut hole of a spiraling plug configuration) designed to be traversed by same delivery catheter, for the placement of one or more downstream occlusive devices relative to the vascular pathology. The catheter is subsequently withdrawn and repositioned for placement of a second proximal device to close the proximal plug aperture. Alternatively one or more distal and subsequently one or more proximal occlusive devices could be delivered via a microcatheter placed through a 5 French inflated balloon catheter, situated proximal to the vascular pathology in order to eliminate or reduce both flow and intravascular pressure (flow arrest). Therefore, a microcatheter deliverable occlusive device placed coaxially through a 5 French balloon catheter could also solve this problem since the occlusive device or devices could be placed distally and then proximally under the condition of flow arrest. A microcatheter deliverable occlusive device or devices placed through a 5 French balloon catheter (under the condition of flow arrest) could also be useful to create a stable intravascular occlusive construct, in the setting of high flow as might be seen in the setting of an arteriovenous fistula.

The present invention contemplates a medical occlusion device that has a plurality of modes of expansion, whereby the occlusion device can assume a variety of shapes each having a respective outer diameter. The modes of expansion are propelled or powered by different structural elements. For instance, an occlusion device pursuant to the present invention can assume a primary shape that is tubular, where the occlusion device has a self-expanding structure typically of shape-memory alloy wires woven into a reconfigurable lattice in the manner of conventional vascular stents. The primary tubular shape may assume on further expansion a secondary shape, for instance, a spiraling or helical configuration, exemplarily under a force exerted by a dedicated shape-memory member such as a wire disposed inside or partially inside the tubular structure.

The present invention contemplates an expandable vascular plug that incorporates thrombogenic materials provided on an uncovered plug scaffolding, an uncovered partially porous plug wall weave or mesh, or a semipermeable covering or plug membrane. The thrombogenic materials change the porosity of the plug wall over time from high to low after initial deployment. Alternatively or additionally, an expandable vascular plug may be provided with a hydrogel coating or a similar material that swells or expands upon contact with blood.

The present invention provides an improved vascular occlusion device and/or an associated surgical method which allows for the placement successive devices in a strategic manner in order to better and more safely treat long segment vascular pathology such as an elongated fusiform aneurysm (endovascular trapping). The method entails placement of an initial proximal occlusive device to reduce inflow to the lesion. The initial proximal occlusive device has a channel or passageway or plug aperture that may be traversed with the same delivery catheter for the placement of one or more downstream secondary occlusive devices relative to the vascular pathology. After the deployment of the secondary occlusive device(s) distal of the first occlusive device, the catheter is withdrawn and used for placement of a final proximal device to close the proximal plug aperture thereby occluding the vascular segment at two ends of sides spaced from one another.

The present invention provides an improved vascular occlusion device and/or an associated surgical method which allows for primary treatment of saccular intracranial or peripheral aneurysms. Two covered or uncovered interlocking or intertwined devices may be assembled within the aneurysm sac to generate aneurysm occlusion and thereby sparing the parent vessel. Obliteration of the aneurysm sac may alternatively be accomplished with a single modified expanding occlusion device, which is tapered at both ends, in essence exhibiting a tapering tubular corkscrew design along both the leading and trailing ends of the occlusive device, thereby approximating a spheroid or ellipsoid shape typical of an aneurysm sac. The device outer wall for this purpose could be uncovered, covered with a microporus membrane, or covered with an impervious membrane.

BRIEF DESCRIPTION OF THE DRAWINGS

The drawings are schematic views of various embodiments of a vascular occlusion device in accordance with the invention, which may be alternatively used in carrying out a method pursuant to the invention.

FIG. 13B shows an internal shape-memory element not depicted in FIG. 13A.

DETAILED DESCRIPTION

The present vascular occlusion device or plug, e.g., plug 20 (FIGS. 1A and 1B), is deliverable through a microcatheter 18, which can occlude a wide range of vessel sizes from small to large, currently not possible with available microcatheter deliverable devices. The design allows for the occlusion of vessels both smaller and larger than 5 mm, the current upper limit for a microcatheter deliverable plug.

Figure 1A:
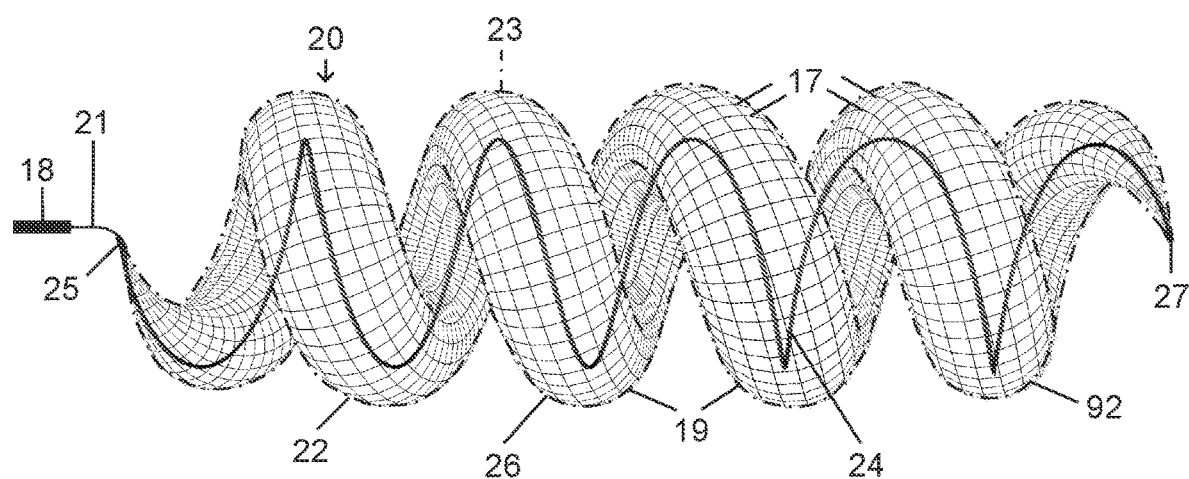
FIG. 1A is a schematic side elevational view of a vascular occlusion device in accordance with the present invention, showing an expanded deployment or use configuration of the vascular occlusion device. The expanded deployment of use configuration of the vascular occlusion device has loops or coils that are axially or longitudinally distracted or spaced as compared to FIG. 1B
Figure 1B:
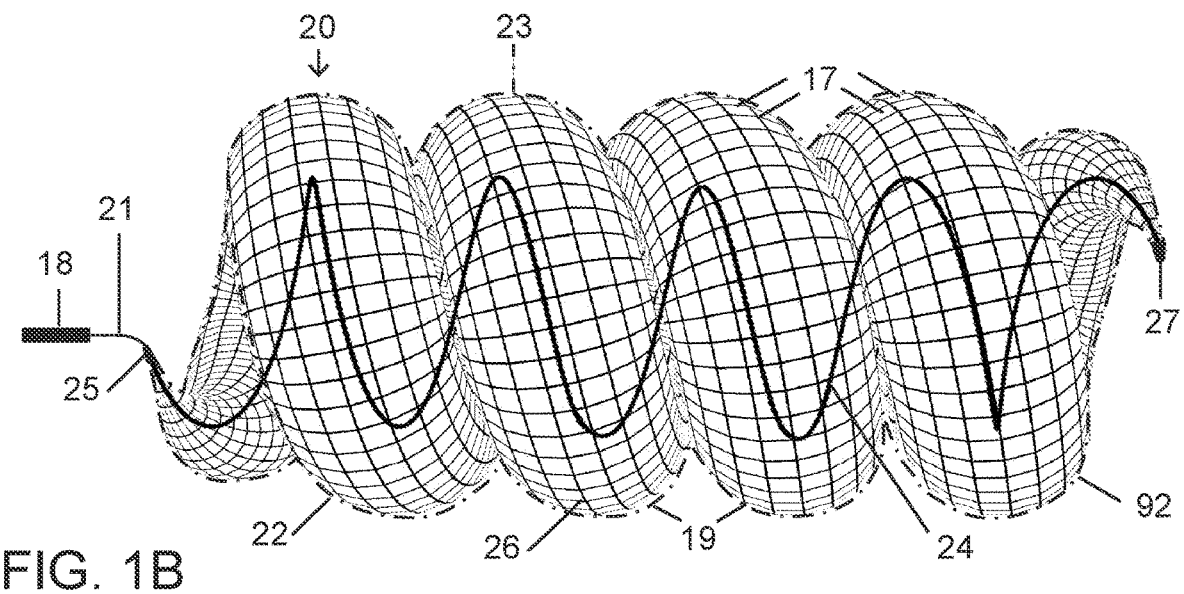
FIG. 1B is a schematic side elevational view of the vascular occlusion device of FIG. 1A, showing another expanded deployment or use configuration of the vascular occlusion device. The expanded deployment of use configuration of FIG. 1B has loops or coils that are axially compacted as compared to FIG. 1A

In an expanded deployment configuration as shown in FIGS. 1A and 1B, a self-expanding and self-configuring vascular plug or occlusion device 20 takes an expanded form of a three-dimensional spiraling tubular structure 22, optionally covered with an impermeable or partially permeable membrane 23, which allows for large vessel occlusion via microcatheter 18, currently not possible with available devices.

FIG. 1A shows relative distraction or separation of coiled segments or windings 19 of plug or occlusion device 20 while FIG. 1B shows relative compaction of the coiled segments or windings 19 of the plug, which might be achieved by retraction or advancement or the deployment wire 21. Microcatheters such as microcatheter 18 are small delivery catheters, usually manufactured with two different size internal diameters, namely 0.021 inch (standard) and 0.027 inch (high-flow). Larger 4 French and 5 French delivery catheters could also be used for delivering even larger diameter vascular plugs, typically having internal diameters of 0.040 inch and 0.046 inch respectively. Therefore the same design could be used for larger 4 and 5 French deliverable devices to occlude even larger arteries, veins, or aneurysms.

Vascular plug or occlusion device 20 includes a primary subunit in the form of self-expanding tubular structure 22 (shown with the beginning of a spiral in FIG. 2) designed to optimize flexibility, conformability, and compressibility. The self-expanding tubular structure 22 is constructed of a shape memory material such as nitinol or other metal alloys. More particularly, tubular structure 22 is a mesh, network or lattice of shape-memory metal wires or strands 17 that are connected to one another and selectively slide relative to one another to enable a change in conformation of tubular member 22 from a tightly drawn, near-linear configuration (not shown) when constrained inside delivery catheter 18 to an expanded tubular form illustrated in FIG. 2. Such lattices are well known in the medical industry as stents are typically made of such structures.

The plug or occlusion device 20 further includes one or more secondary subunits that are elongate shape-memory shaping wires 24 (FIGS. 1A, 1B, 3) made of a stiffer coiling metal alloy, exemplarily nitinol. Each shaping wire 24 longitudinally traverses the primary covered tubular subunit or structure 22 in order to form or force the tubular subunit 22 into a spiraling or helical configuration 92 (FIGS. 1A, 1B) which is inherently of larger diameter than primary subunit or tubular structure 22 (FIG. 2) and provides an enhanced or increased outward radial force for pressing the primary subunit or tubular structure 22 against an endothelial surface and maintaining the plug or occlusion device 20 at a desired or target vascular location.

The ability of device 20 to form itself into both the primary tubular shape of subunit 22 (FIG. 2) and the secondary spiraling or helical configuration 92 (FIGS. 1A, 1B) allows for the treatment of a wide range of vessel sizes with a single device. The unique shape memory and superelasticity of nitinol alloys are ideal for creating the secondary spiraling or helical configuration 92 (FIGS. 1A, 1B) and generating outward radial force sufficient to anchor the vascular plug or occlusion device 20 to the endothelium of a target blood vessel in opposition to the downstream-directed force exerted on the device during implantation, which depends in part on the permeability of any membrane 23 covering the device.

The coiling nitinol shaping wire or wires 24 may be fully incorporated into a wall 26 of plug or occlusion device 20, for instance, woven together with wires or strands 17 into the mesh or lattice of tubular structure 22, or freely floating in a lumen thereof, or partially incorporated into or attached at two or more spaced points to a lattice wall 26 of tubular structure 22. Exemplarily, each shaping wire 24 may be connected to end or closure points 25 and 27 of tubular structure 22. Under its own internal forces, body or wall 26 of the tubular structure 22 exerts enough radial force to maintain the primary tubular shape but is flexible enough to assume the spiraling or helical configuration 92, in response to the stronger spring force of the one or more incorporated coiling nitinol shaping wires or spines 24.

Figure 6:
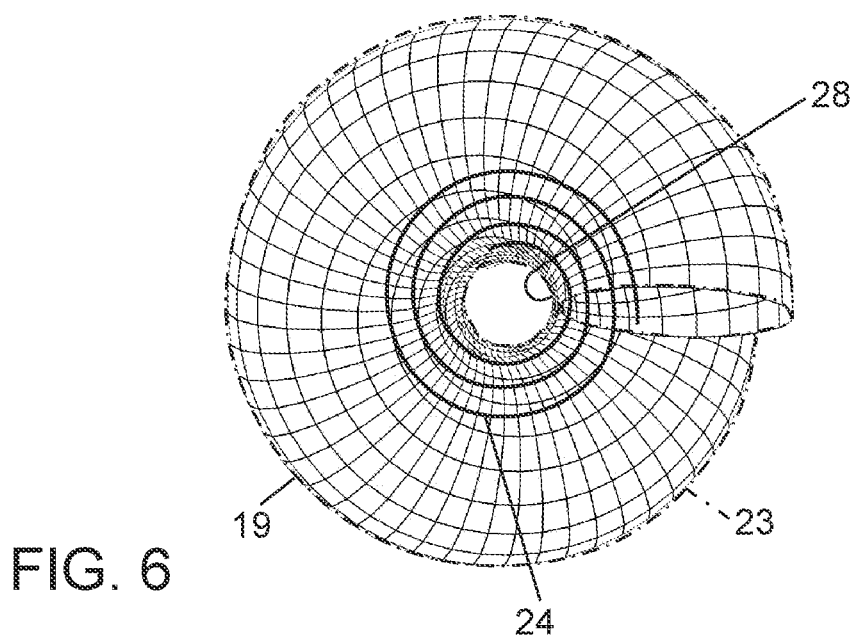
FIG. 6 is an end elevational of the device of FIG. 4.

Preferably, device 20 includes a single shaping wire 24 that forms an inner or small-diameter curve of spiraling or helical configuration 92 (see FIGS. 1B and 6). That one shaping wire 24 is preferably attached to tubular structure 22 at ends 25 and 27 and is interwoven or partially interwoven into the lattice of tubular wall 26 or alternatively is free within the lumen of the tubular structure 22. The internal spring forces of wall 26 maintain the tubular structure 22 in an open tube form and together with shaping wire 24 maintain the spiraling or helical secondary configuration 92. The nitinol shaping wire 24, incorporated into plug or occlusion device 20, contributes substantially to the creation of outward radial force needed for device anchoring in addition to formation of the secondary shape, i.e., spiraling or helical configuration 92.

If a target vessel is too small for the self-expanding tubular subunit 22 to form the larger secondary spiraling or helical configuration 92 (FIGS. 1A, 1B) the at least one internal spiraling wire or spring memory element 24 still serves a critical function, namely, increasing the radial force exerted on tubular structure 22 of the device 20 for better vessel anchoring. Flexibility and conformability of the primary self-expanding tubular subunit or structure 22 is needed to create the spiraling, twisting or helical configuration 92 of the tubular secondary design structure. Compressibility of the tubular subunit or structure 22 either in a substantially cylindrical or minimally coiled configuration (FIG. 2) or in the expanded or secondary spiraling or helical configuration 92 (FIGS. 1A, 1B) is desirable to accommodate different vessel sizes.

Figure 14A:
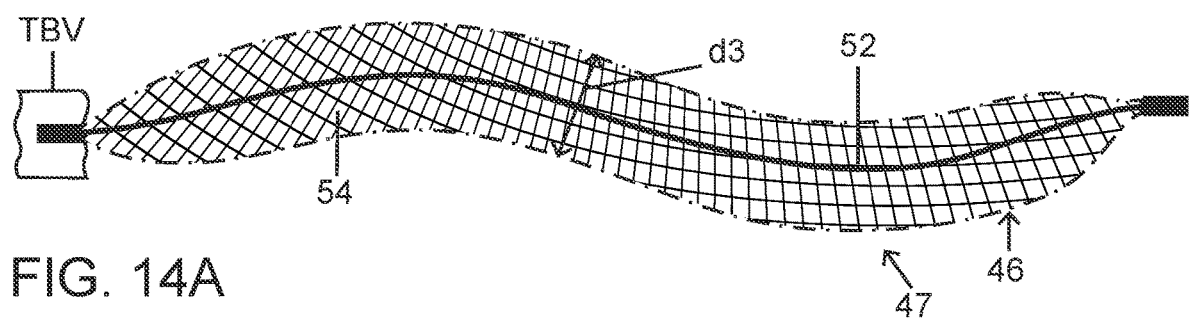
FIGS. 14A, 14B and 14C are respective side elevational views of a vascular plug or occlusion device in accordance with the present invention, showing different states or degrees of secondary expansion or twisting as determined by the size or diameter of a vascular lumen in which the plug or occlusion device is deployed.
Figure 14B:
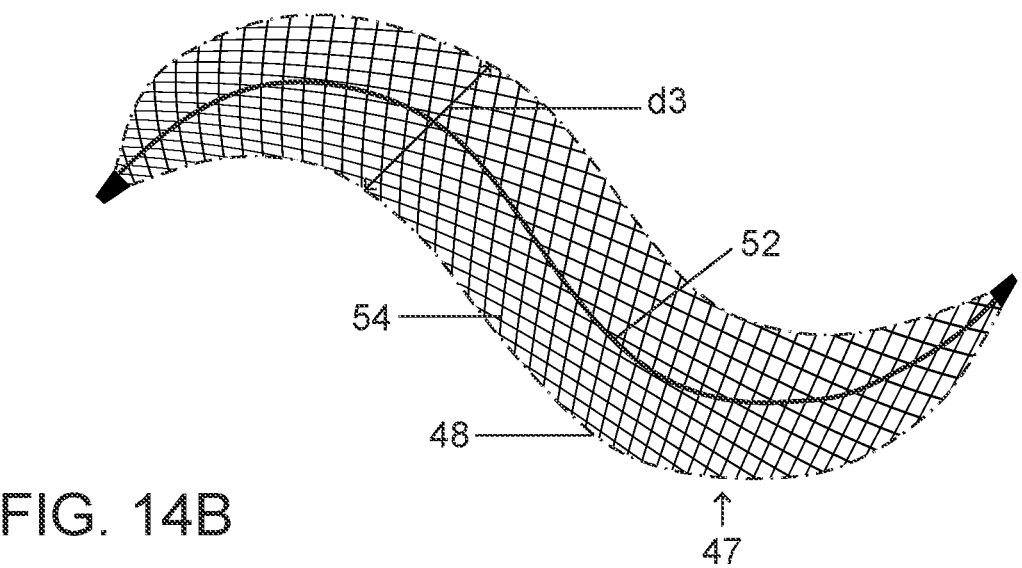
Figure 14C:
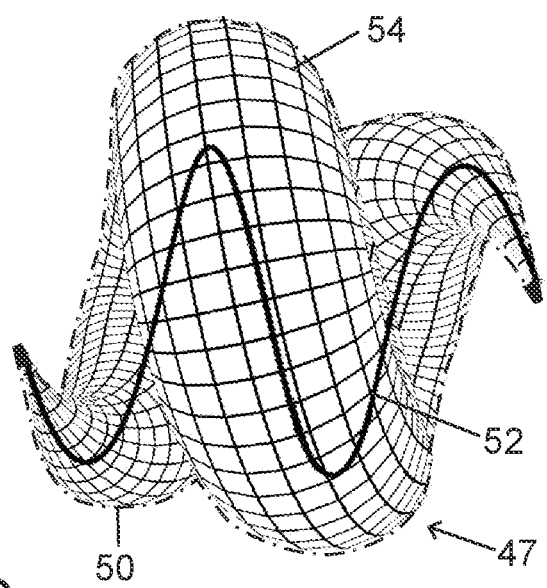

The body or wall 26 of tubular structure 22 may be laser cut from a nitinol tube or created from braided or woven wire strands 17 made from nitinol or other suitable metal alloy including but not limited to a Cobalt-Chromium alloy. A braided plug outer wall 26 comprised of wire strands 17 woven together may include a Platinum-Tungsten alloy to increase the radio-opacity of the device, critical for identifying the primary and secondary shapes the device might assume depending on the vessel diameter (FIG. 14A-C).

Figure 4:
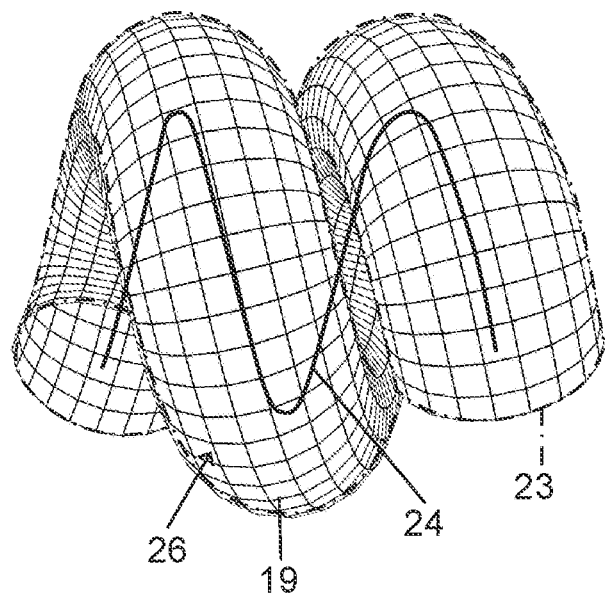
FIG. 4 is a side elevational view, on a larger scale, of a portion of a vascular occlusion device in accordance with the present invention, showing a shape-memory coil incorporated into the wall or within the lumen of a tubular body.

A braided design of plug wall 26 allows for increased flexibility, conformability, and compressibility to facilitate the creation of the secondary plug shape, spiraling or helical configuration 92 (FIG. 4). In addition to the method of plug body construction and design, the alloys constituting the plug body and particularly the outer wall 26 thereof may be chosen to optimize the same characteristics. A braided plug body or wall 26 might also facilitate partial or complete incorporation of the coiling nitinol shaping wire 24 directly into the weave or braid of the plug wall 26 as opposed to the alternative design of being free within the plug lumen. The shaping wire may be fixed or able to move or slide relative to its attachment or anchoring points within the plug wall or along its inner surface.

Where vascular plug or occlusion device 20 includes membrane covering 23, that membrane can be made of, but not limited to, PTFE, Teco Thane, nylon, PET, Carbothane (Bionate), fluoropolymer, SIBS, and PGLA. The primary tubular plug subunit or structure 22 is preferably covered with an impervious membrane 23 except for an uncovered downstream terminal end, allowing blood to enter and exit the plug body, thereby facilitating plug repositioning or removal prior to final mechanical detachment. An upstream portion of the plug covering 23 is preferably impervious to flow while a terminal downstream section of the plug or occlusion device 20 may be porous or uncovered.

Figure 17A:
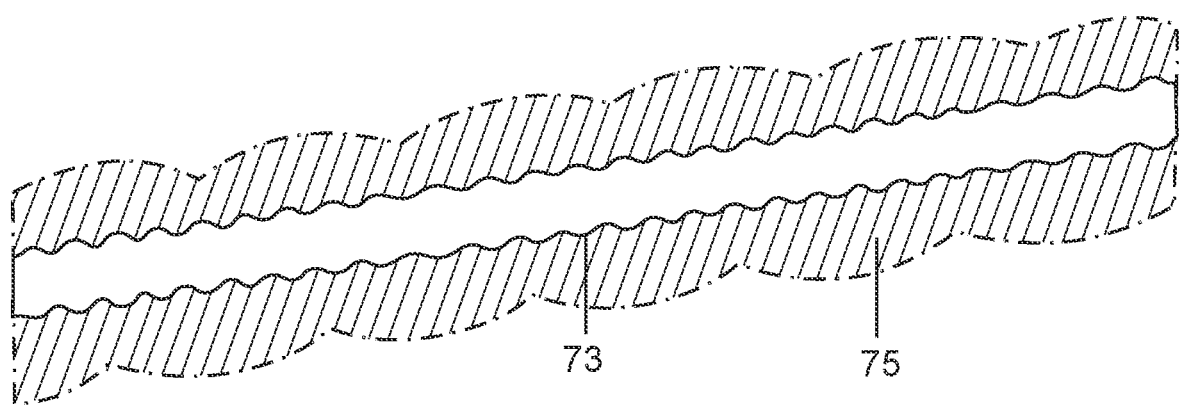
FIG. 17A is coil covered with expanding hydrogel in clinical use.
Figure 17B:
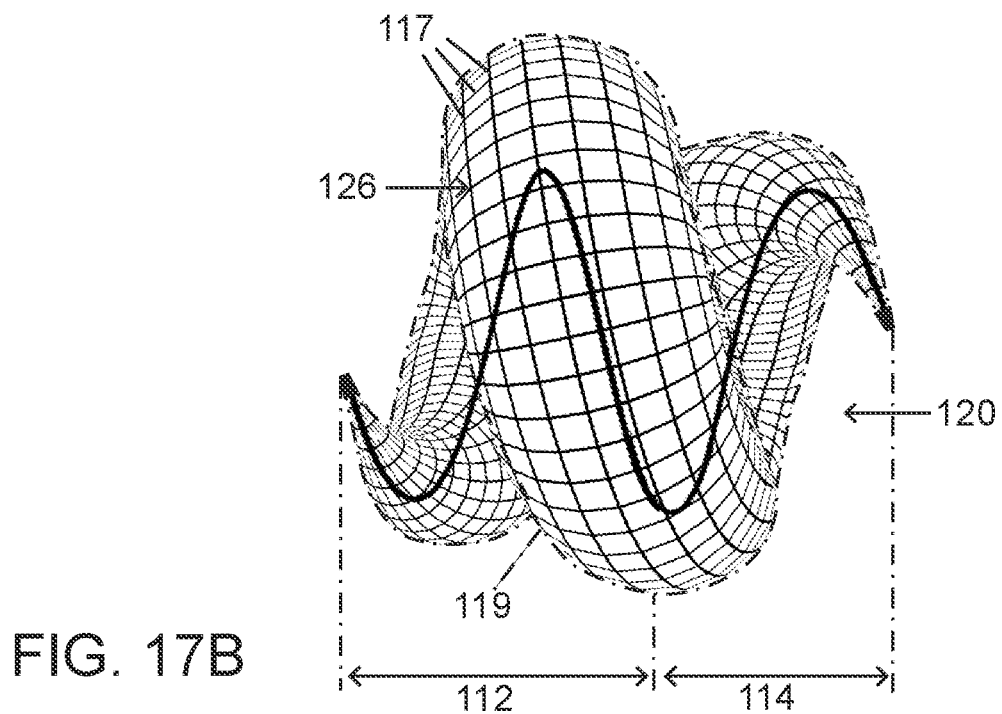
FIG. 17B is a uncovered spiraling vascular plug or occlusion device in accordance with the present invention.

In another vascular plug or occlusion device 120, a plug body wall 126 is uncovered (FIG. 17B). An upstream portion 112 of vascular plug or occlusion device 120 has a low porosity to promote stasis and thrombosis, while a downstream portion 114 has a higher porosity to allow for blood flow into and out of a plug lumen (not designated), enabling repositioning or removal of device 120 prior to final deployment thereof.

Any plug or occlusion device 20 disclosed herein that has a very low porosity is more thrombogenic while plugs or occlusion devices 20 with a higher porosity are less susceptible to migration under the conditions of high flow; higher porosity enables the operator to create an initial stable construct or scaffolding with one or more uncovered plugs 20, with subsequent placement of one or more covered or very low porosity devices 20 in order to complete vessel occlusion. Changing the weave pattern in the plug wall 26 or utilizing a porous plug covering or membrane 23 could change the porosity of the plug wall 26.

Figure 16A:
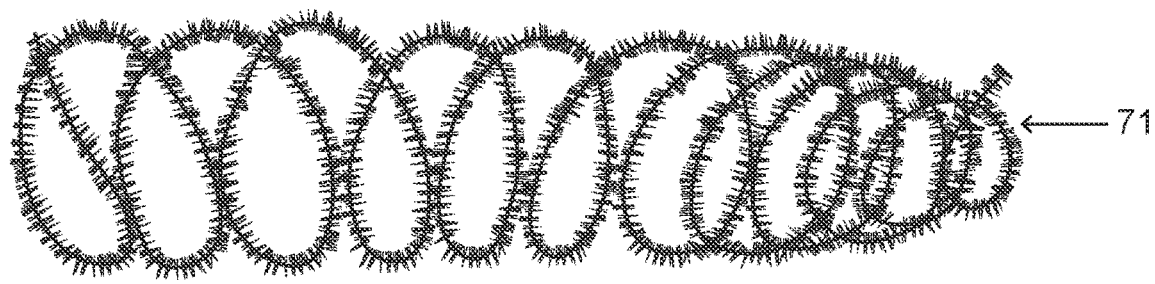
FIG. 16A is a traditional fibered coil in clinical use.
Figure 16B:
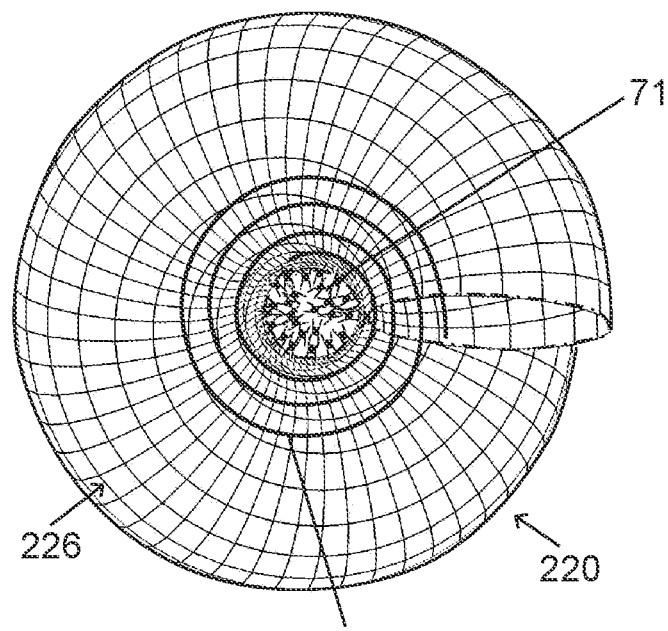
FIG. 16B is an end view of a fully formed covered plug spiral containing central thrombogenic fibers to promote closure of the patent central channel or "doughnut hole" pursuant to the present invention.
Figure 16C:
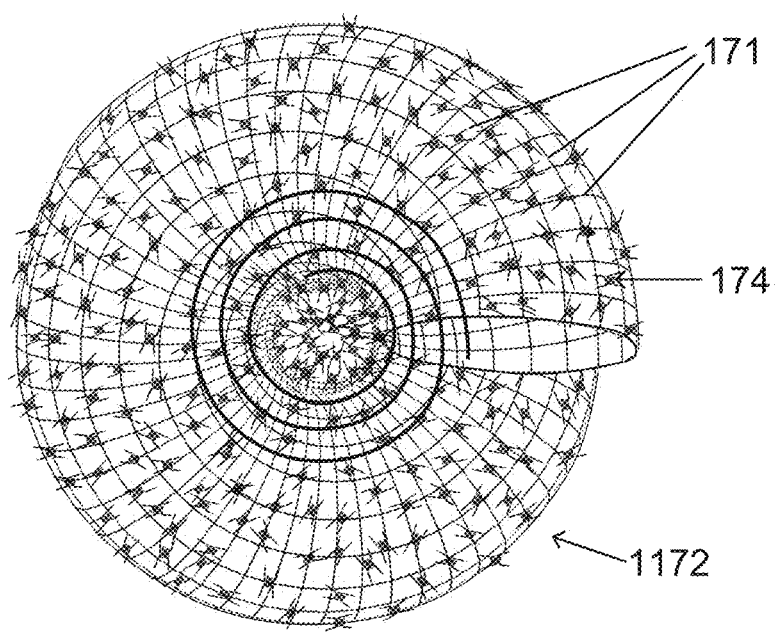
FIG. 16C is an end view of a fully formed uncovered plug spiral with thrombogenic fibers distributed through interstices of the plug.

In another vascular plug or occlusion device 220 (see FIGS. 16B, 16C, 17A), a plug body wall 226 is not covered with an impervious membrane but is instead coated with various thrombogenic materials including but not limited to small fibers 71 (FIG. 16B) or hydrogel 75 (FIG. 17A) to engender vessel thrombosis. Thrombogenic fibers 171 may be distributed throughout the interstices in a wall 174 of an uncovered plug 172, as shown in FIG. 16C, in order to promote vessel thrombosis.

A coil 73 covered in hydrogel 75 is depicted in FIG. 17A. As shown in FIG. 17B, braided or woven wires 117 of plug or occlusion device 120 may be coated with hydrogel 119 in a similar fashion. An uncovered plug 120 coated with hydrogel 119 or a similar substance may be of value in high flow situations to prevent device migration with vessel thrombosis occurring after a period of time. A hydrogel-coated plug 20 or 120 might be useful in a high flow setting allowing time for deployment of two stable interlocking devices 20 or 120 prior to the assembled construct becoming impervious to flow, with the devices 20 or 120 being inserted either simultaneously via two delivery catheters or in succession via one catheter, the hydrogel 119 decreasing the chances of device migration (FIGS. 9, 10, 11, 12, 13). A commercially available hydrogel coating expands by 80% within three minutes and reaches maximal expansion 20 minutes after coming in contact with blood. Swelling of hydrogel 75 results in a 3-4 times increase in the effective size of a traditional coil 73 relative to a baseline (FIG. 17A).

Tubular structure 22 of vascular plug or occlusion device 20 is inserted in a collapsed form (FIG. 2) into a proximal end (not shown) of delivery catheter 18 (FIGS. 1A, 1B) with a tapered introducer (not shown) and advanced through the catheter with a pusher wire 21. This procedure is performed after the catheter is in place, with the distal tip (not designated) located at or near a target device deployment site, and a conventional guidewire (not shown) is removed. Once the plug or occlusion device 20 reaches the distal end of the delivery catheter 18 the plug is unsheathed, for instance, by pulling back the delivery catheter 18 while simultaneously fixing or holding the pusher wire 21. This method for the insertion of plug or occlusion device 20 into catheter 18 and ejection therefrom is applicable to any of the plugs or occlusion devices described herein.

One of many well-known mechanical (threaded or interlocking, for example) or electrolytic detachment mechanisms may be provided and utilized to release the plug 20 after formation of the desired primary or secondary shapes. This method for the detachable coupling of plug or occlusion device 20 to pusher wire 21 is applicable to any of the plugs or occlusion devices described herein. The plug or occlusion device 20 device could be withdrawn and removed prior to final detachment for any reason, including but not limited to inappropriate sizing.

Figure 2:
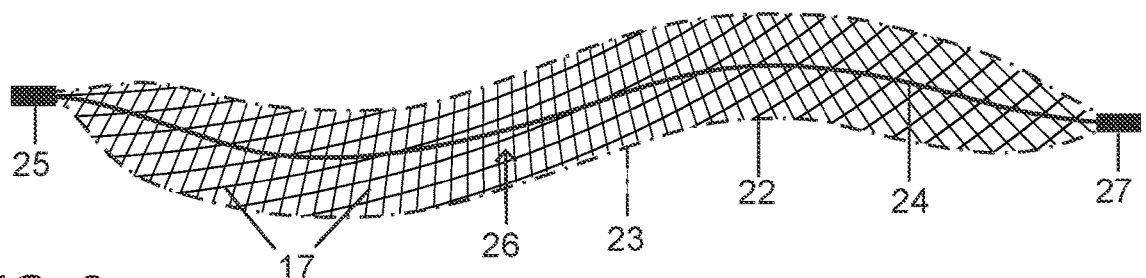
FIG. 2 is a side elevational view of the vascular occlusion device of FIGS. 1A and 1B in a tubular, extended, and slightly coiled configuration suitable for collapse and insertion into a deployment microcatheter.
Figure 3:
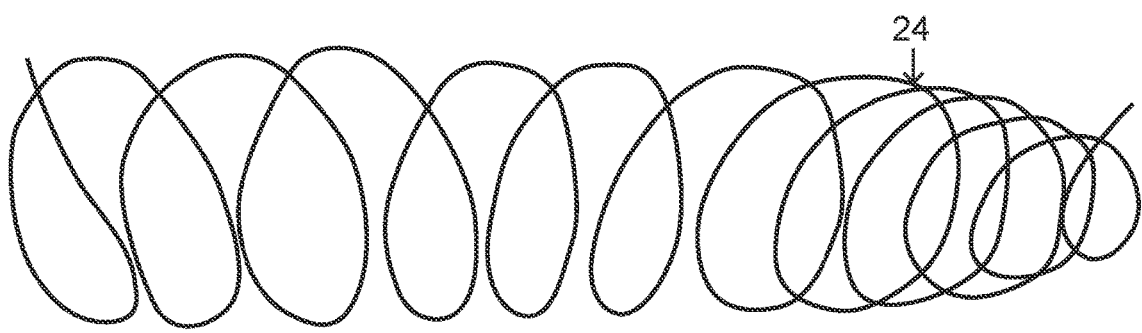
FIG. 3 is a side elevational view of a shape-memory spiral-forming wire element included in the vascular occlusion device of FIGS. 1A and 1B.
Figure 5:
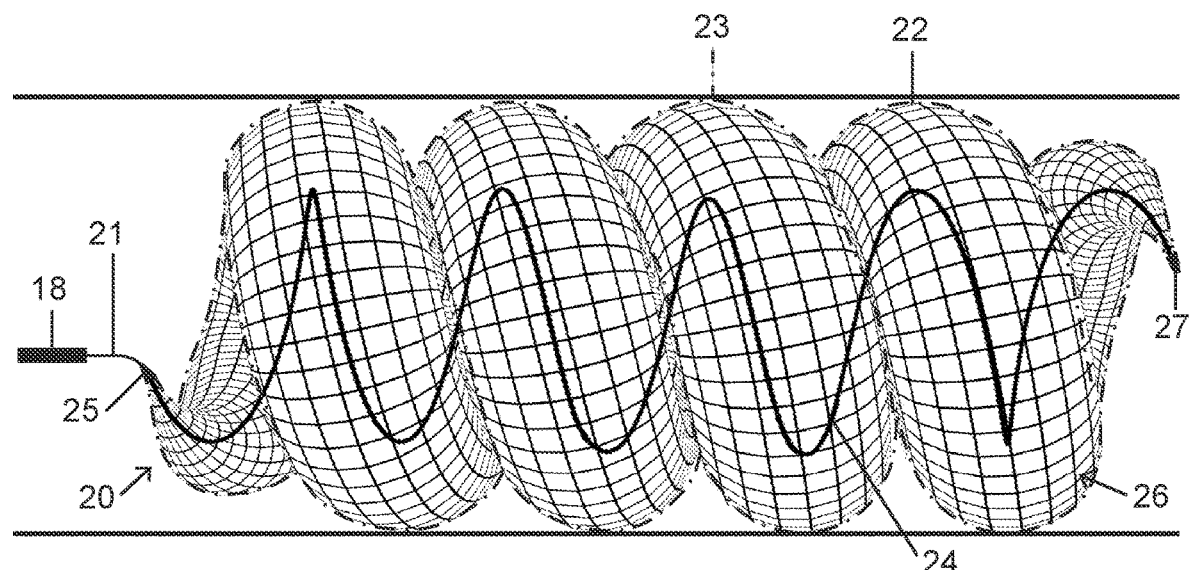
FIG. 5 is a side elevational view of a vascular plug or occlusion device essentially identical to that of FIGS. 1A, 1B, showing the device inside a schematically depicted blood vessel.

The plug or occlusion device 20 may be made in various diameters and lengths depending on the clinical purpose or vascular pathology. The overall diameter of a fully formed spiraling or helical configuration of plug or occlusion device 20 (FIGS. 1A, 1B, 5) may be greater than two times the diameter of the cylindrical plug subunit or tubular structure 22 (FIG. 2). For example, a 4 mm diameter tubular plug 22 would have greater than an 8 mm overall outer diameter when fully formed into the coiled or spiraling shape (FIGS. 1A, 1B, 5), likely in the range of at least 10 mm. The outer diameter of a plug or occlusion device in fully formed spiraling or helical configuration 92 (FIGS. 1A, 1B) constitutes two diameters of subunit or tubular structure 20 plus a width of a central patent channel or passageway 28 (FIG. 6), which is preferably less than the diameter of an individual primary tubular subunit or structure 22. The formation and diameter of patent central channel 28 varies based on parent vessel size, primary device diameter and compressibility of the overall plug configuration.

Figure 7A:
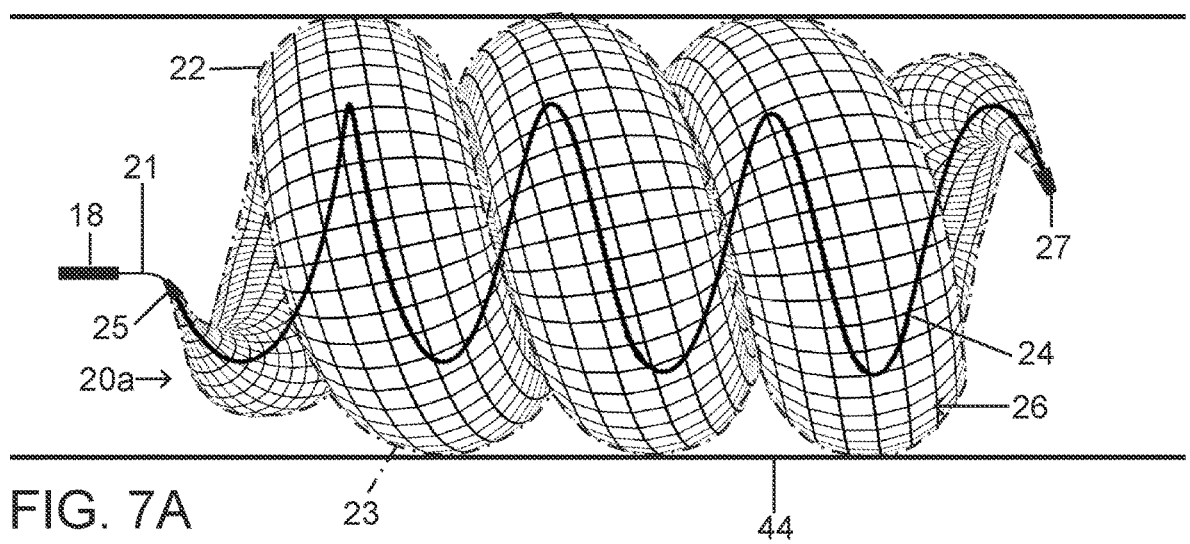
FIGS. 7A and 7B are schematic side elevational views of a vascular plug or occlusion device in accordance with the present invention, showing different numbers of turns of the spiraling body member owing to different lengths thereof.
Figure 7B:
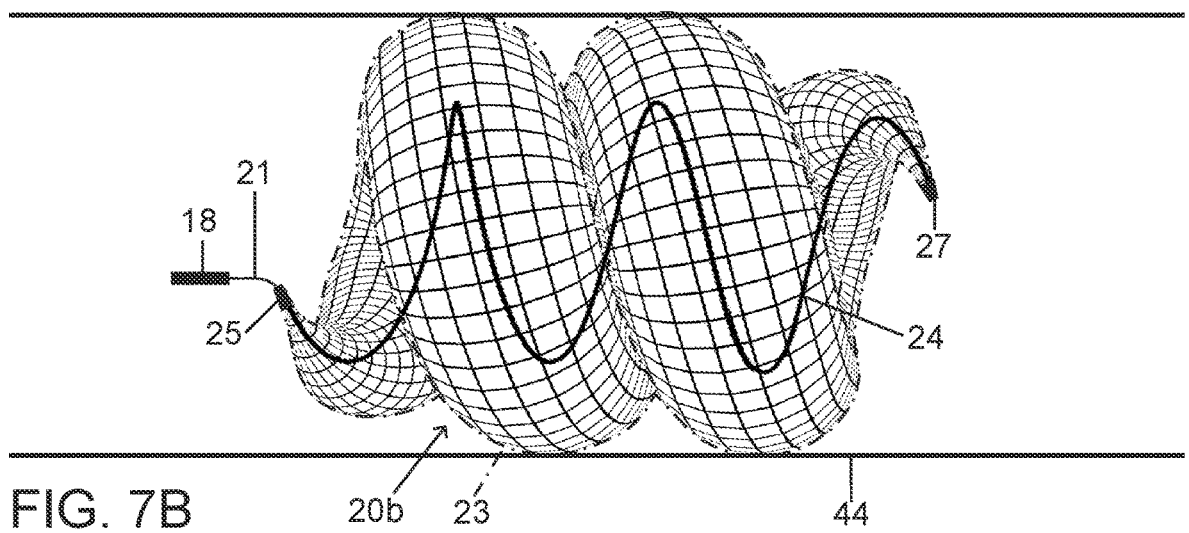
Figure 8:
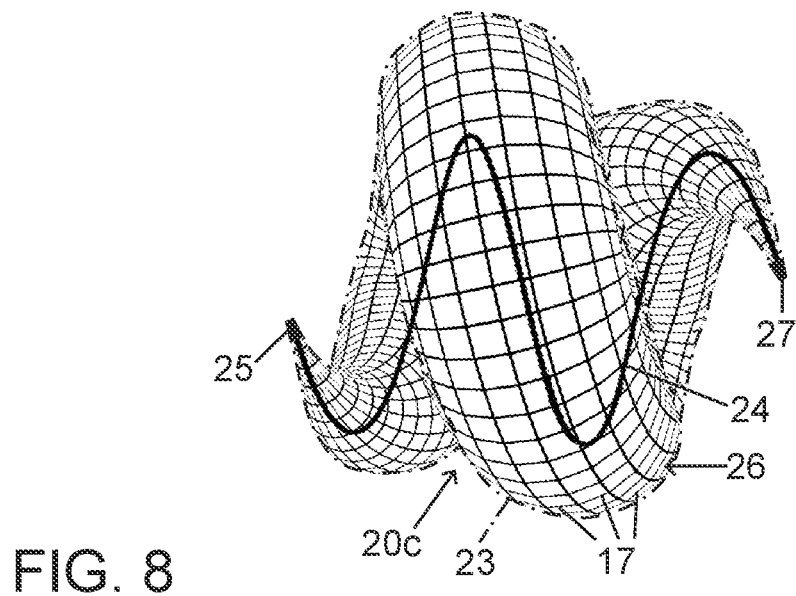
FIG. 8 is a schematic side elevational view of a short vascular plug with a minimum number of spiraling turns in an expanded configuration, pursuant to the invention.
Figure 9:
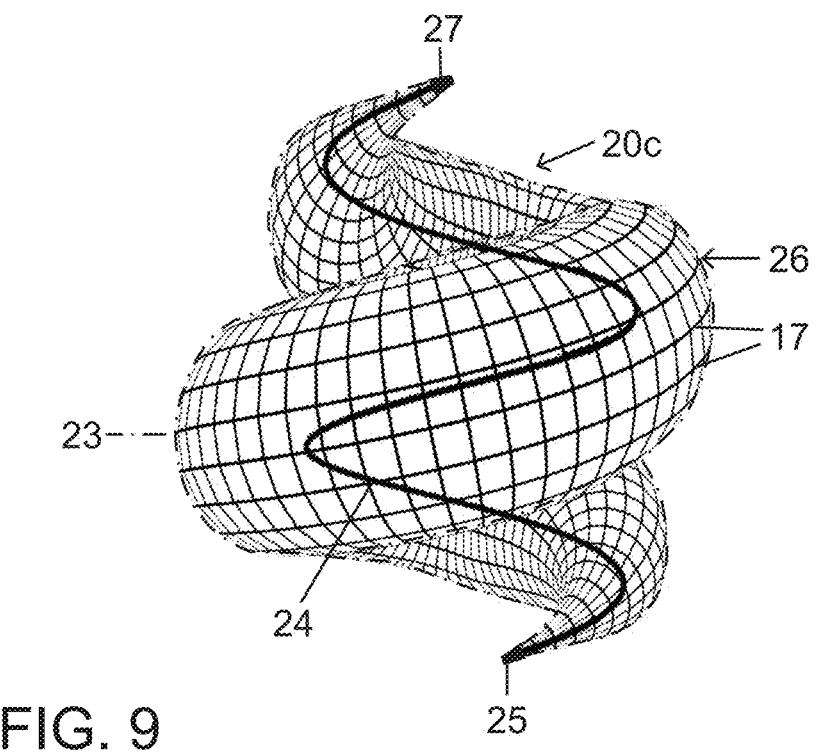
FIG. 9 shows the plug of FIG. 8 in a different orientation.

Different lengths of plug or occlusion device 20, or of the primary subunit or tubular structure 22 (FIG. 2) in its uncoiled configuration may be provided based on the clinical indications. Occluding segmental vascular pathology or large fusiform aneurysms would benefit from a longer device 20a (FIG. 7A). In other applications, a shorted device 20b (FIG. 7B) is indicated. The minimum length to achieve the fully formed secondary spiraling or helical shape is dictated by the length that is required for a plug or occlusion device 20c to form a single 360 degree spiral (FIG. 8).

Figure 10:
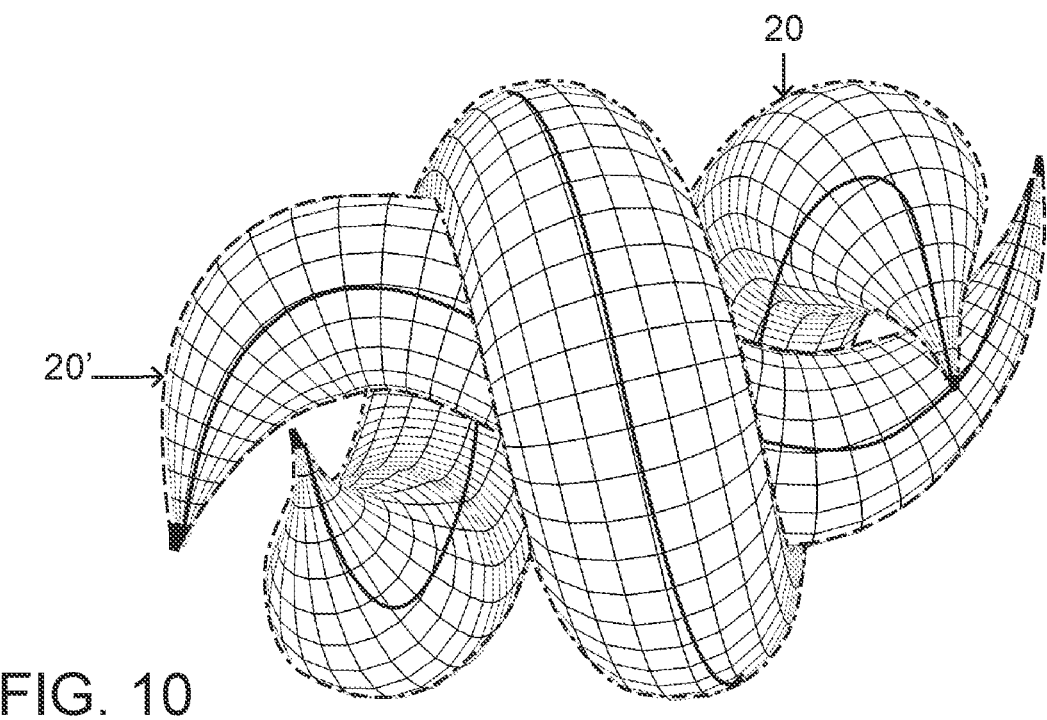
FIG. 10 is a schematic side elevational view of a pair of intertwining and interlocking short vascular plugs, in accordance with the invention.
Figure 11A:
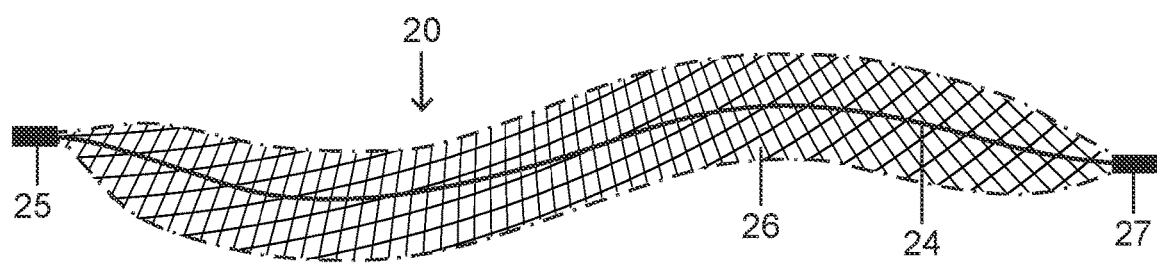
FIG. 11A is a side elevational view of the vascular occlusion device of FIGS. 1A and 1B in a slightly coiled configuration.
Figure 11B:
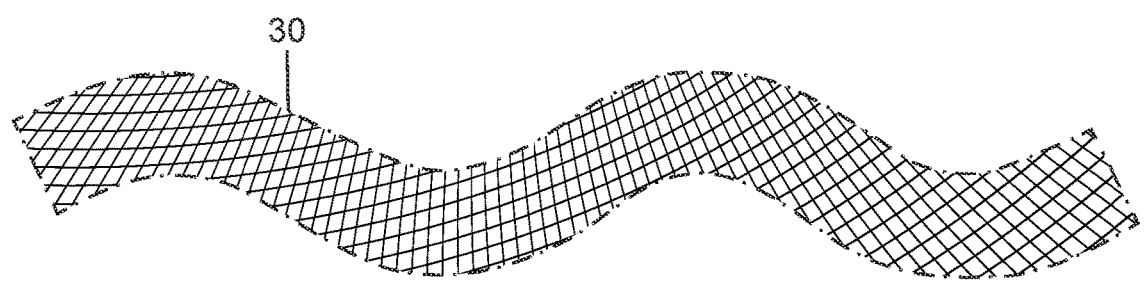
FIG. 11B is a partial side elevational view of vascular occlusion device in a partially expanded and partially spiraling configuration, occurring in vessels too small to permit complete expansion.

Compaction of the occlusion device 20 (or any modification thereof described herein) after initial deployment (prior to release) may be achieved with the delivery wire 21, creating the fully formed secondary shape from a partially twisted configuration depending on the parent vessel size. Delivery wire 21 is urged in a distal direction pushing proximally located coils of the spiraling or helical configuration 92 or turns toward more distally positioned coils or turns. Different degrees of compaction of the device 20 in the fully expanded spiraling or helical configuration 92 are depicted in 1A and 1B. A patent central channel or "doughnut hole" passageway 28 may be created by a fully formed coiled or spiraling plug 20 (see FIG. 6) that is provided with a covering or membrane 23, where the target blood vessel is sufficiently large. The potential central channel or "doughnut hole" passageway 28 may be occluded with a second plug or occlusion device 20' creating an even more stable occlusion assembly (FIG. 10). Alternatively coils could be used for this purpose depending on the amount of residual flow and the size of the patent central channel or passageway 28 (FIG. 6).

In another version of a vascular plug or occlusion device 220 (FIG. 16B), thrombogenic fibers 71 are incorporated into the outside surface of the plug wall 26 to help close the patent central channel or "doughnut hole" passageway 28. Thrombogenic fibers 71 may be attached to the spiraling nitinol coil or secondary subunit 24 incorporated into the plug wall 26, forming the inside curve of the spiraling or helical configuration 92 (see FIGS. 1A and 1B), strategically positioning the fibers 71 into the central channel or passageway 28 (FIG. 6) promoting luminal thrombosis (FIG. 16B).

Figure 12:
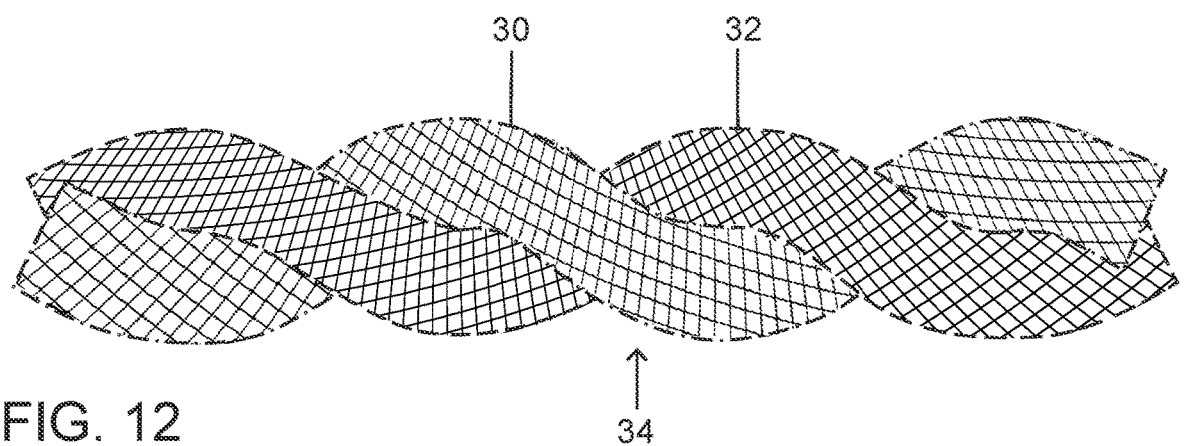
FIG. 12 is a partial side elevational view of a pair of partially expanded vascular occlusion devices in a double helix configuration, deployed to adequately occlude vessels larger than the primary device diameter but smaller than the fully expanded secondary diameter.
Figure 13A:
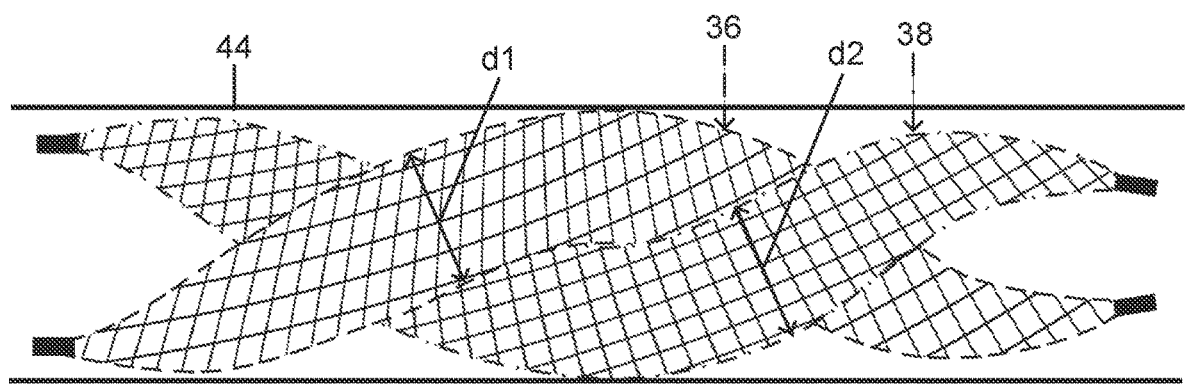
FIGS. 13A and 13B are side elevational views of a pair of plugs or vascular occlusion devices deployed in tandem to occlude a vessel too small to permit full expansion of either plug or device, similar to FIG. 12.
Figure 13B:
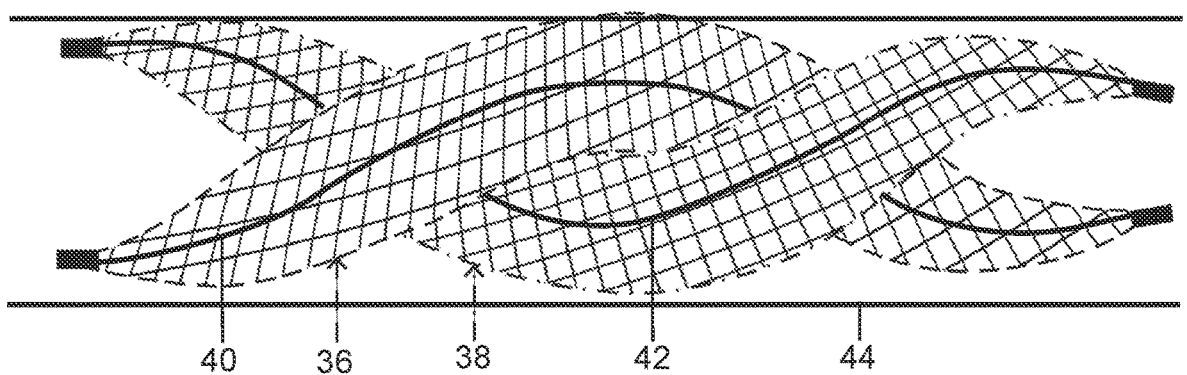

The presence of the central channel or passageway 28 is advantageous in high flow situations in allowing for the creation of a more stable final superstructure or assembly, preventing migration of a first inserted vascular plug or occlusion device 20, prior to final occlusion with a second device 20' (FIG. 10; see also FIGS. 12, 13A, 13B). Placement of a device 20 in a vessel slightly larger than the diameter of the primary subunit or tubular structure 22 can result in a partially twisted or spiraling secondary shape 30 (FIG. 11B), which might result in some residual flow around the device. Complete occlusion is achieved by traversing the first deployed plug 30 with the same delivery microcatheter 18 (see FIGS. 1A, 1B) with placement of a second parallel partially spiraling plug or occlusion device 32 that interlocks with the first device 30 to create a double helix configuration 34 (FIG. 12).

FIGS. 13A and 13B depict two intertwined vascular plugs or occlusion devices 36, 38 of the above-described type each with a shape-memory wire or spine element 40, 42 (FIG. 13B) that tends to form the respective device into a spiraling or helical configuration. Devices 36 and 38 are of identical or different diameters d1 and d2 and are deployed in succession, preferably via the same microcatheter, to achieve closure of a vessel 44 greater than the diameter d1, d2 of either device 36, 38 but too small to form a maximal secondary spiraling shape of a size sufficient to occlude the vessel.

Alternatively, if a target blood vessel TBV is smaller than an uncoiled tubular structure 46 of a primary plug or occlusion device 47 (FIG. 14A), then neither a partially coiled (FIG. 14B) or a fully expanded twisting shape (FIG. 14C) can form and occlusion is achieved by solely by an uncoiled or essentially straight configuration of primary vascular plug or occlusion device 47. Overall device configuration in the deployed occlusion state therefore depends on target vessel size at the site of implantation. The primary tubular shape or structure 46 is retained in an essentially linear or straight form upon deployment of the plug or occlusion device 47 in vessels of a diameter less than the diameter d3 of the primary plug or occlusion device 47 (FIG.

14A). Vascular plug or occlusion device 47 is biased to attain a twisted or helical configuration 50 (FIG. 14C) in response to an outward force exerted by a shape-memory nitinol wire or spine 52 within the plug wall 54 or within the lumen of the device. The twisting and curving range of secondary configurations 48 of a partially expanded vascular plug or occlusion device 47 (FIG. 14B) makes the device ideal for placement in curved vessels or vascular segments, where it conforms to the overall vessel shape and course. A partially twisted or partially expanded spiraling configuration 48 of the vascular plug or occlusion device 47 is naturally formed in vessels greater than the diameter d3 of vascular plug or occlusion device 47 (FIG. 14A) but less than or equal to twice the diameter d3, possibly requiring a second parallel device 47 (to create a double helix configuration) or coil placement to eliminate any residual flow (FIG. 14B). A completely formed spiraling or helical configuration 50 of vascular plug or occlusion device 47 (FIG. 14C) is formed in vessels somewhat greater than twice the diameter d3 and might require a second centrally placed device or coil 47 to eliminate any residual flow, this contingency being depicted in FIG. 10, showing two plugs or occlusion devices 20 and 20' with device 20 being deployed and expanded into a spiraling or helical form as shown and plug 20' subsequently inserted inside an aperture of passageway (not designated) extending through a center of the spiraling configuration of deployed device 20.

Figure 15:
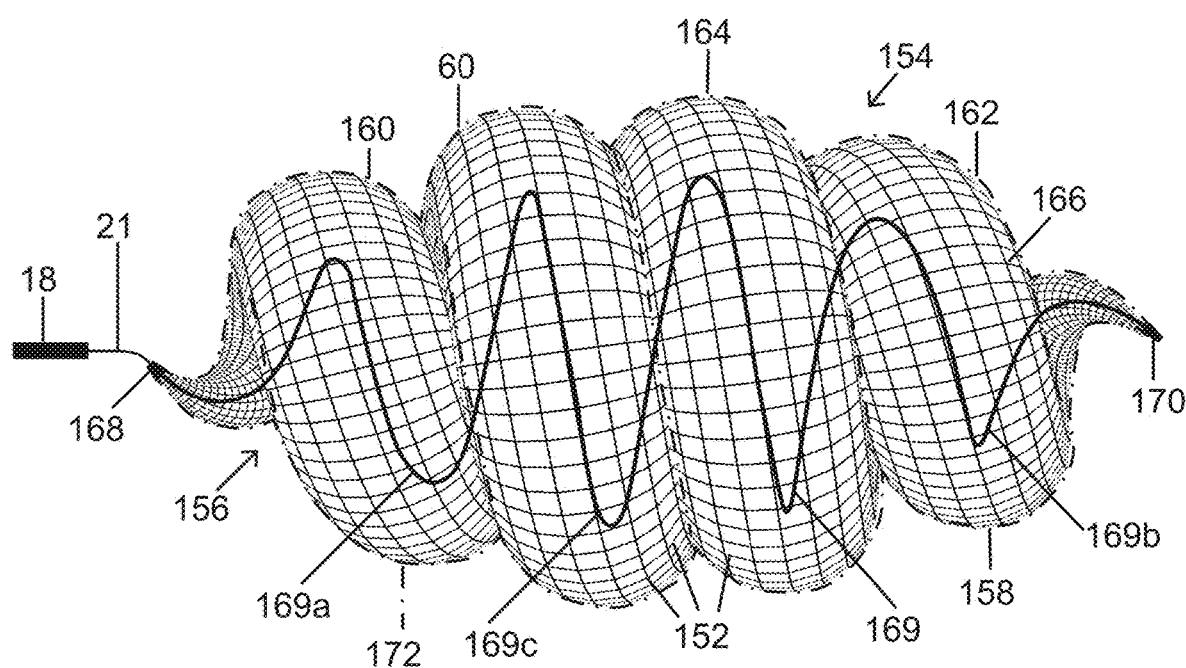
FIG. 15 is a side view of a tapering spiral plug or modified corkscrew design, which minimizes or eliminates the patent central channel of a fully formed plug.

It is to be noted that a vascular plug or occlusion device 154 may be designed to have a fully expanded spiraling or helical configuration that is tapered at opposite ends 156 and 158 as depicted in FIG. 15, which tapering minimizes or eliminates a patent central channel or "doughnut hole." Thus, in the fully expanded spiraling or helical configuration, vascular plug or occlusion device 154 has proximal and distal turns 160 and 162 that have smaller outer diameters than a longitudinal midpoint or center turn 164 of the device 154. At opposing ends, an outer wall 166 of the device tapers to closure or terminal points 168 and 170. A shape memory spiral-forming wire or spine 169 is connected at its opposite ends to closure or terminal points 168, 170. Like other versions of a vascular plugs or occlusion devices described herein, plug or device 154 may be provided with a covering or outer membrane 172 that may be impermeable or partially permeable in part or throughout, depending on the application. Plug or occlusion device 154 incorporates spiral-forming wire or spine 169 that has, in its fully formed spiraling conformation, terminal portions or windings 169a and 169b that are of reduced diameter relative to a middle portion or middle windings 169c.

Figure 18A:
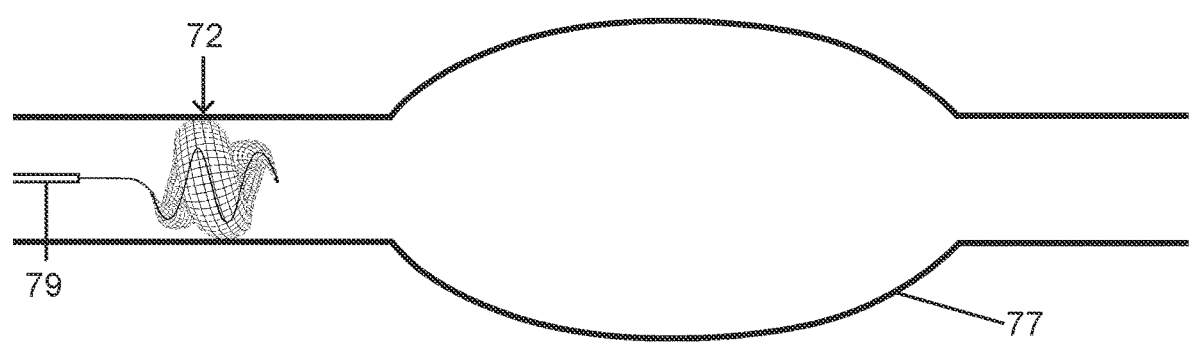
FIGS. 18A-18D depict successive stages in a surgical procedure to isolate a fusiform aneurysm, utilizing vascular plugs or occlusion devices in accordance with the invention, in a method pursuant to a feature of the invention.
Figure 18B:
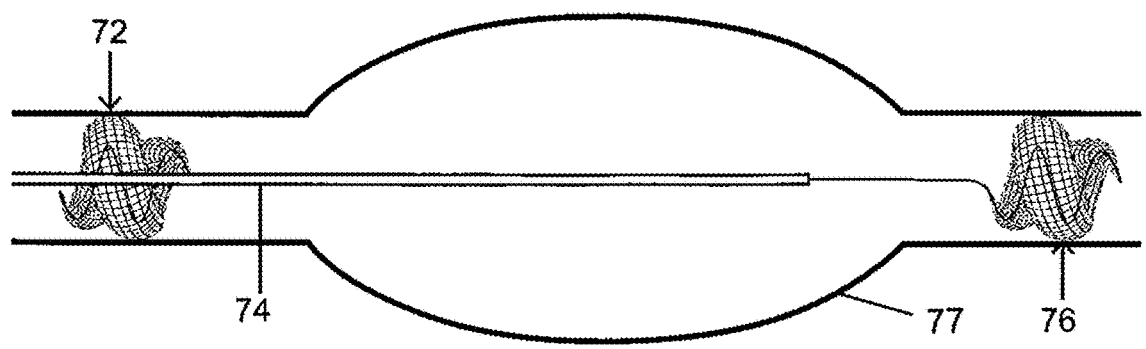
Figure 18C:
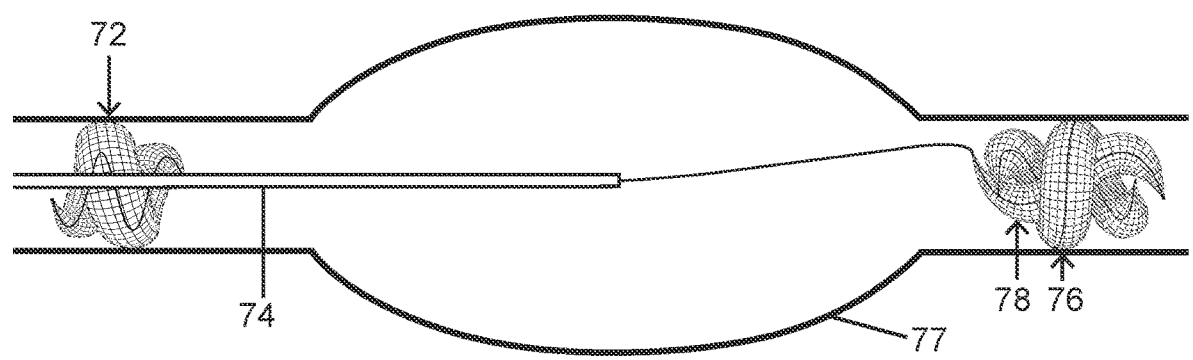
Figure 18D:
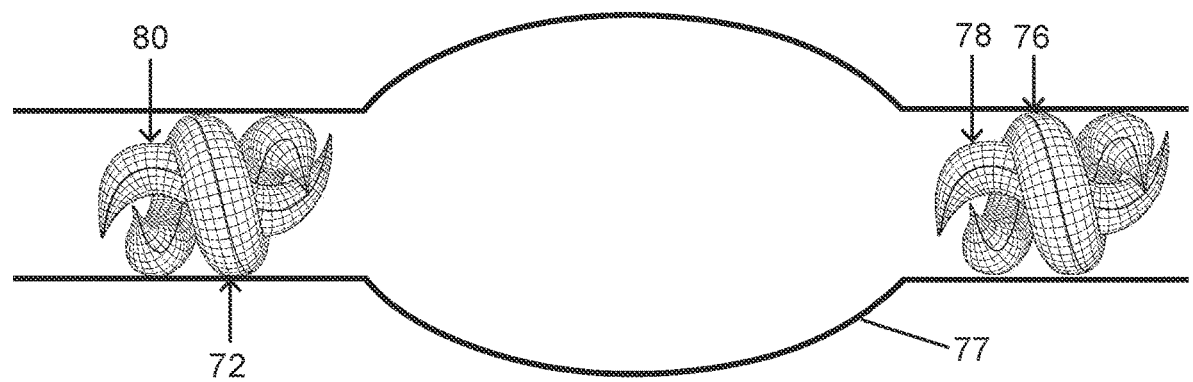

In the treatment of segmental vascular pathology, particularly useful for long segment vascular disease such as an elongated fusiform aneurysm 77 (FIGS. 18A-18D), it is contemplated to place successive vascular plugs or occlusion devices 72, 76, 78, 80 in a strategic manner (e.g., endovascular trapping); this is accomplished by placement of an initial proximal occlusive device 72 with a spiraling or coiled expanded configuration as shown in FIG. 18A, to reduce inflow to the aneurysm or lesion 77. Possible delivery catheters 79 include: microcatheters with internal diameters of 0.021 inch (standard) and 0.027 inch (high-flow) as well as larger 4 French and 5 French delivery catheters for deploying even larger diameter vascular plugs, typically having internal diameters of 0.040 inch and 0.046 inch respectively. Occlusive device 72 is designed to be traversed through a plug aperture, channel or passageway 28 (patent central channel or space around a partially twist device, as shown in FIG. 6) with the same delivery catheter 79 or a second delivery catheter 74 (FIGS. 18B and 18C) for the placement of one or more downstream occlusive devices 76 and 78 relative to the vascular pathology or aneurysm 77. Subsequently the catheter 79 or 74 is withdrawn through the plug aperture, channel or passageway 28 of the first placed, proximal occlusion device 72 and used for placement of a final second proximal device 80 to close the aperture, channel or passageway 28 of the proximal occlusion device (FIG. 18D). Vascular plugs or occlusion devices 72, 76, 78, 80 may all have a spiraling or helical expanded configuration (not separately designated) and an internal spine 24 (see FIGS. 1A, 1B, etc.) that is straight in a collapsed configuration of the respective plug or occlusion device 72, 76, 78, 80 inside catheter 79 or 74 and that shapes an expanding tubular outer wall 26 into the spiraling or helical deployed use configuration 92 (FIGS. 1A, 1B). While plugs or occlusion devices 72, 76, 78, 80 are depicted as having fewer than two full (360°) turns or windings in the expanded spiraling or helical configuration (not separately designated), it is to be understood that any of the devices may have more turns or windings. For instance, devices 72 and 76 may have three full turns while devices 76 and 78 have two turns.

Figure 19A:
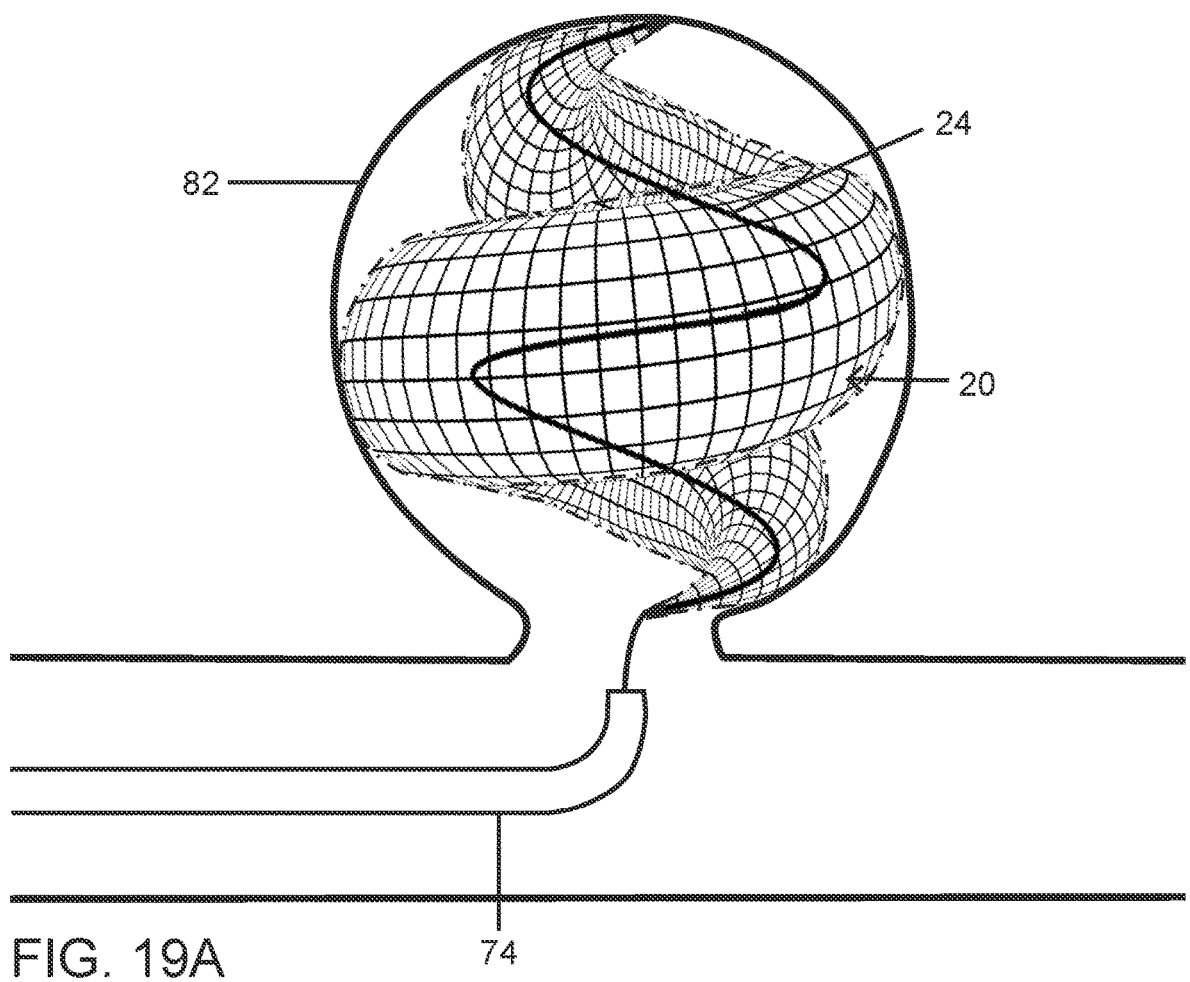
FIG. 19A is a schematic longitudinal cross-sectional view of a blood vessel with a saccular aneurysm arising from it, depicting one deployed plug or occlusive device within the aneurysmal sac.
Figure 19B:
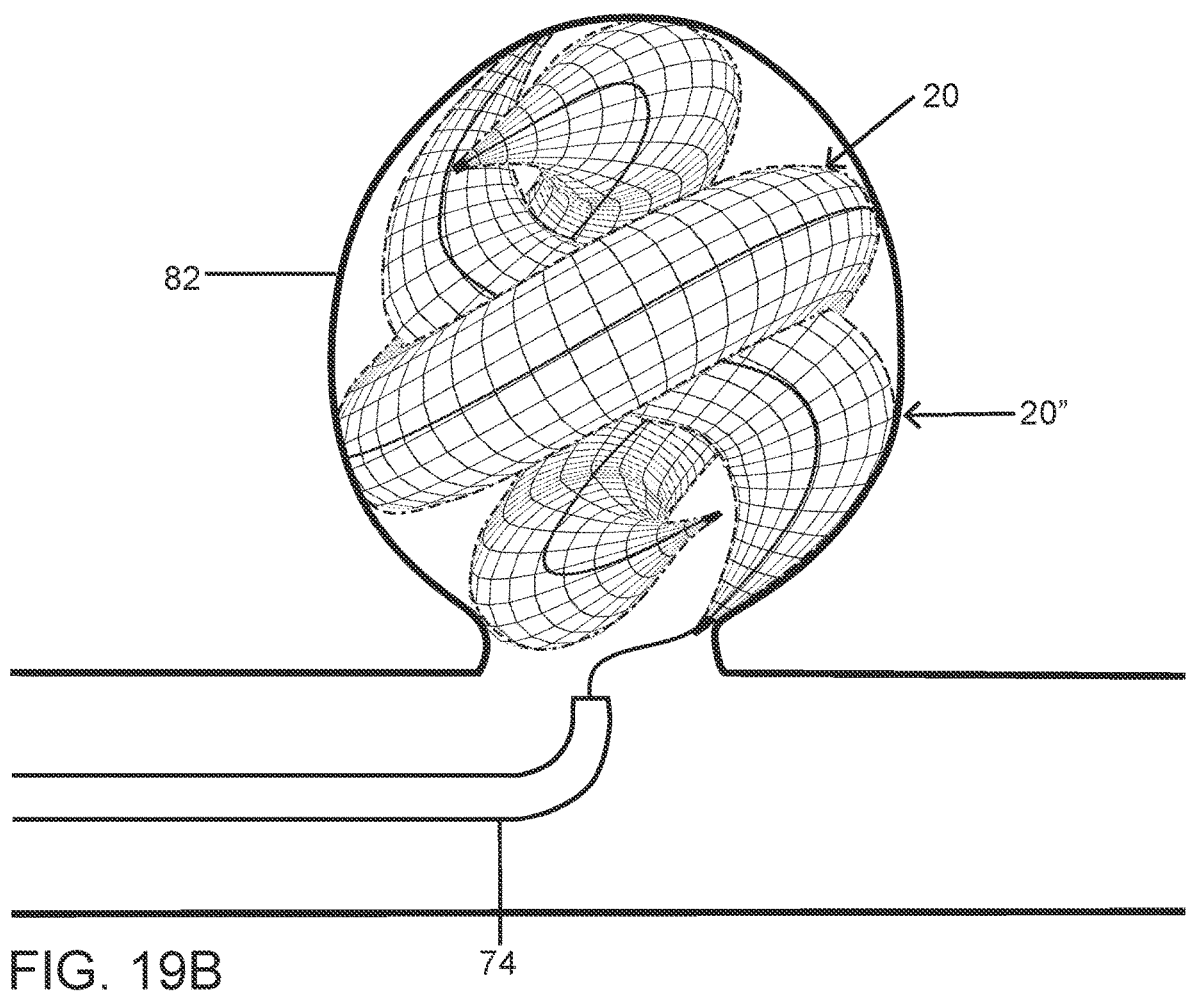
FIG. 19B is a schematic longitudinal cross-sectional view of a blood vessel with a saccular aneurysm arising from it, depicting two deployed interlocking or intertwined plugs or occlusive devices within the aneurysmal sac.
Figure 20A:
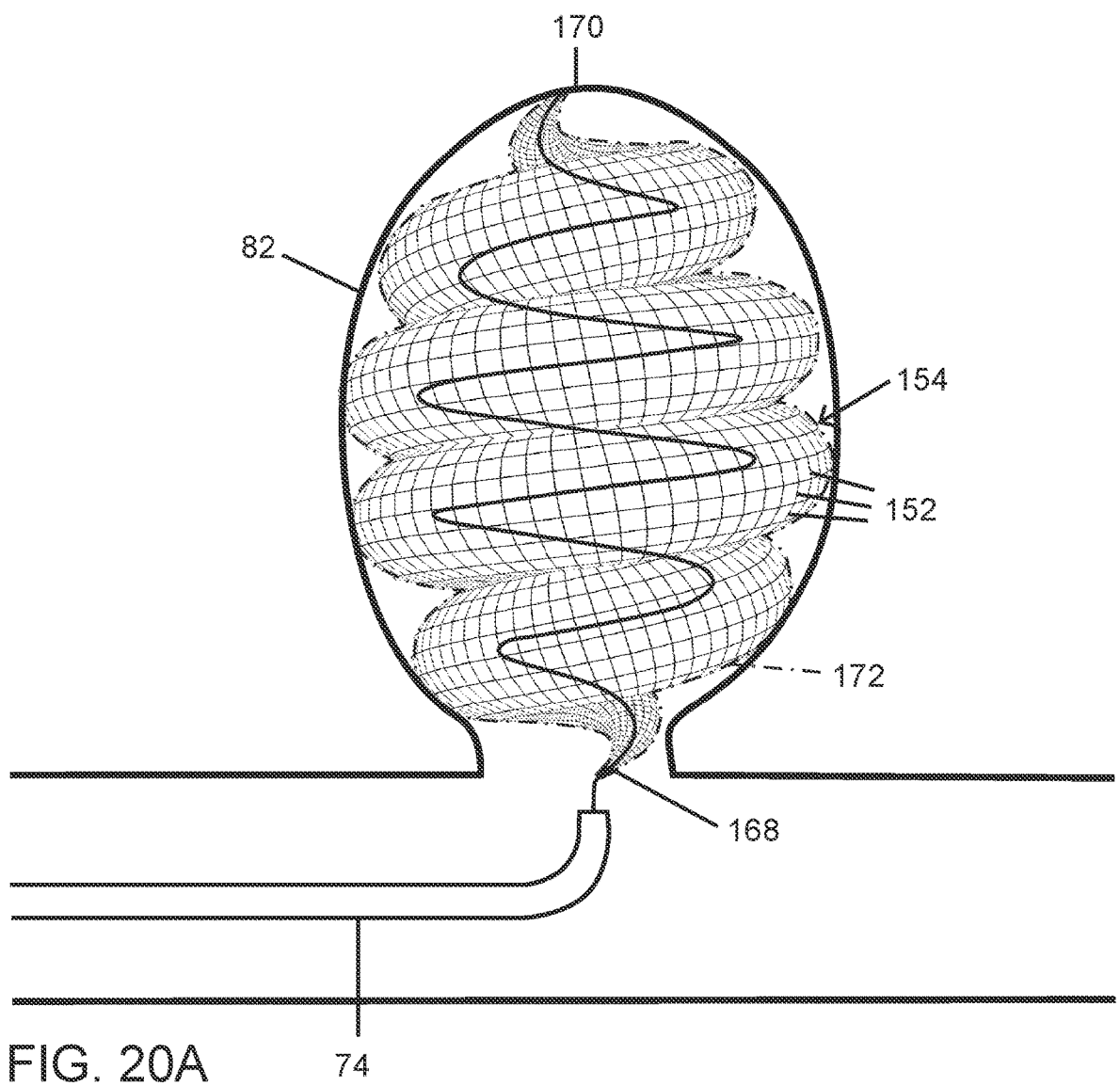
FIG. 20A is a schematic longitudinal cross-sectional view of a vessel with a saccular aneurysm arising from it, containing a longer single deployed modified corkscrew tapering occlusive device in order to obliterate a saccular aneurysm with more of an ellipsoid shape.
Figure 20B:
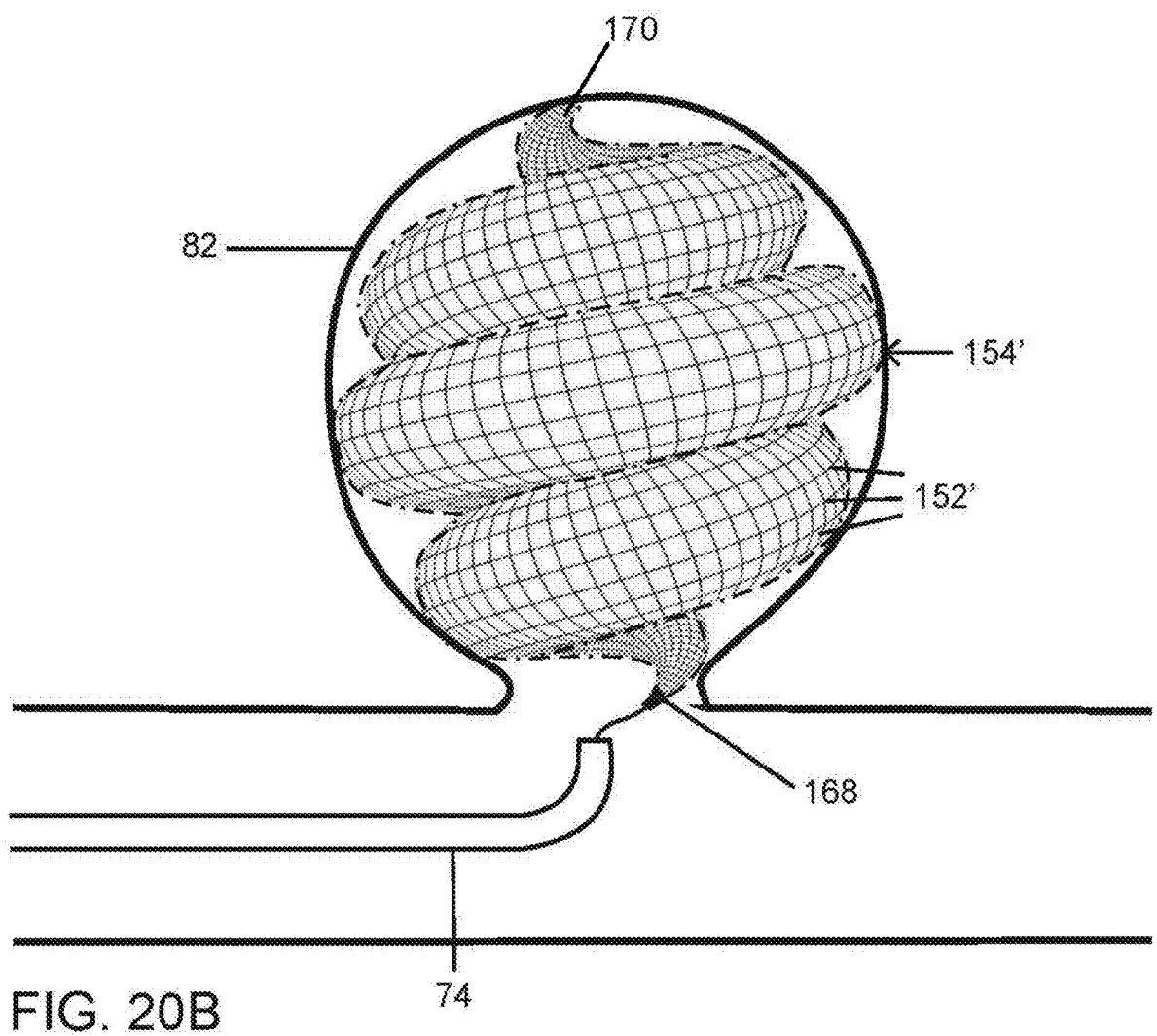
FIG. 20B is a schematic longitudinal cross-sectional view of a vessel with a saccular aneurysm arising from it, containing a shorter single deployed modified corkscrew tapering occlusive device in order to obliterate a saccular aneurysm with more of a spherical shape.

As depicted in FIGS. 19A, 19B, 20A, 20B, vascular plug or occlusion device 20 in one form or another also allows for primary treatment of saccular aneurysms 82. Instead of parent vessel occlusion one or possibly two (covered or uncovered) interlocking or intertwined occlusion devices 20 may be assembled within aneurysm sac 82 (FIG. 19B), resulting in aneurysm occlusion, thus sparing the parent vessel. FIG. 19A shows the deployment of a single device 20 having about a single 360° winding or turn within saccular aneurysm 82. FIG. 19B shows the additional deployment of a second intertwined device 20" such that the two devices together 20 and 20" obliterate or close off the aneurysm sac 82. As illustrated in FIG. 20A, obliteration of the aneurysm sac 82 can also be accomplished with plug or occlusion device 154 (see also FIG. 15), which tapers at both ends 168 and 170 as shown in FIGS. 15 and 20A. In essence plug or occlusion device 154 evinces a tapering tubular corkscrew design along both the leading end 170 and trailing end 168 of the occlusive device 154, and thereby can approximate a spheroid or ellipsoid shape typical of an aneurysm sac 82 depending on length of the sac. A shorter device 154' as depicted in FIG. 20B more closely approximates a spherical shape while a longer device 154 as depicted in FIG. 20A more closely approximates an ellipsoid shape. The devices are transported delivered through appropriate vessels of a patient's vascular system via catheter 74 and ejected into saccular aneurysm 82 where expansion is automatically implemented via the internal spring stresses of interwoven and relatively sliding shape-memory alloy wires or strands 152, 152' of plugs or occlusion devices 154, 154'.

Figure 21:
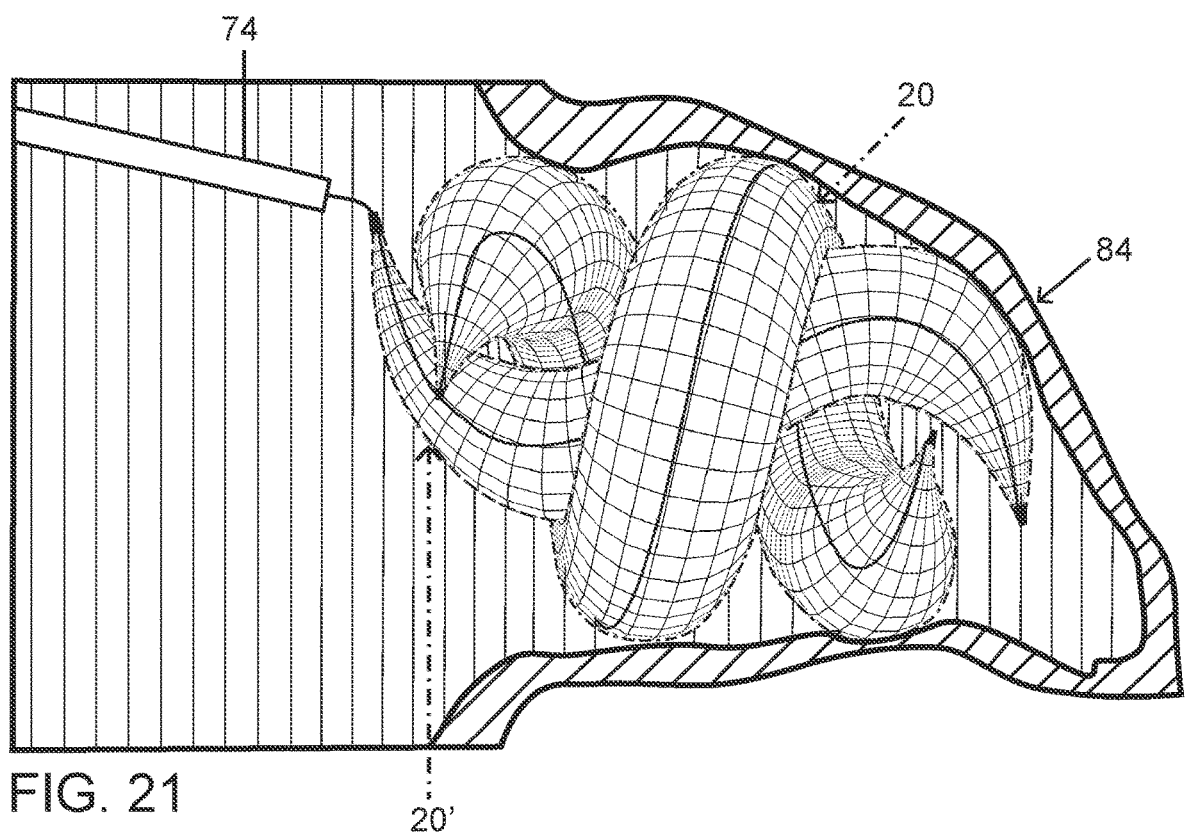
FIG. 21 is a schematic longitudinal cross-sectional view of the left atrial appendage of the heart containing two successively deployed interlocking or intertwined vascular occlusive devices in order to occlude or obliterate the left atrial appendage in accordance with the invention, in a method pursuant to a feature of the invention.
Figure 22:
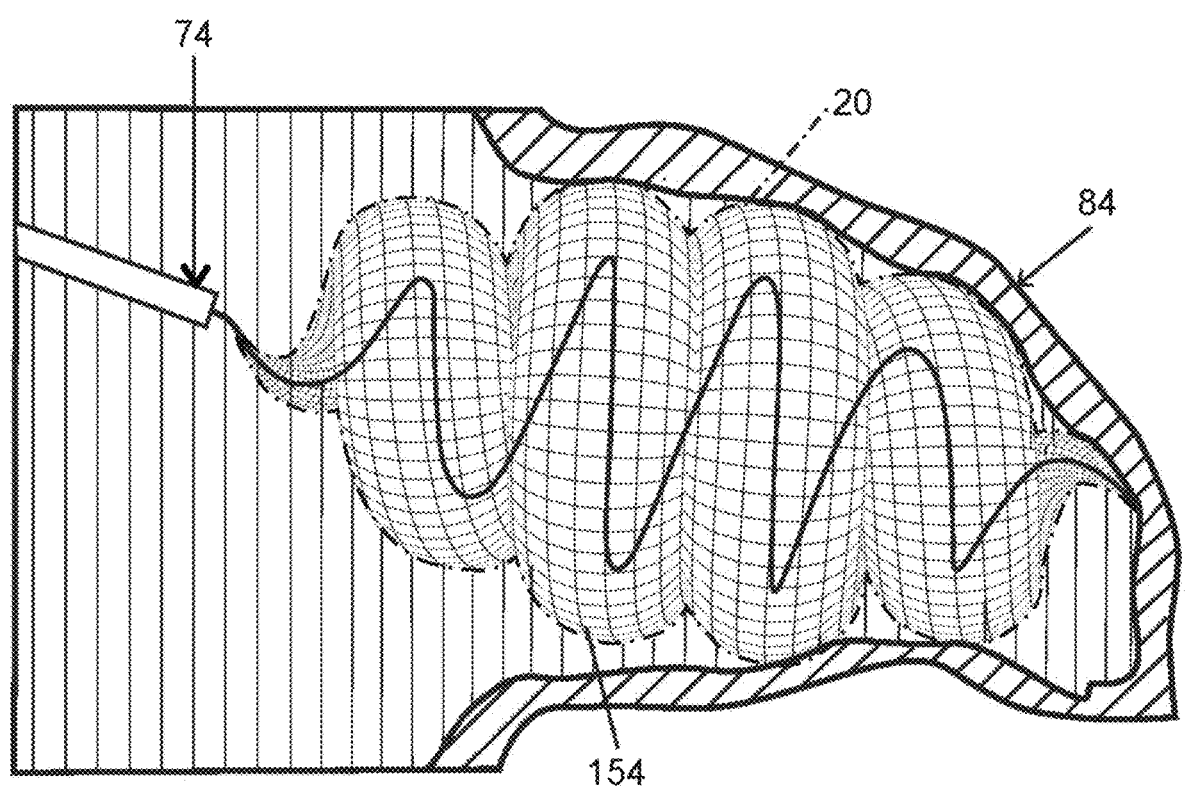
FIG. 22 is a schematic longitudinal cross-sectional view of the left atrial appendage of the heart containing a single deployed modified occlusive device in order to occlude or obliterate the left atrial appendage in accordance with the invention, in a method pursuant to a feature of the invention. The modified occlusive device tapers at both ends, in essence a tapering tubular corkscrew design along both the leading and trailing ends of the occlusive device, thereby approximating the conical or ellipsoid shape typical of the left atrial appendage of the heart.

As depicted in FIG. 21, two devices 20 and 20' may be assembled to one another to form an interlocking or intertwined unit to obliterate a large vascular space such as the left atrial appendage 84 in the clinical setting of atrial fibrillation of FIG. 21. Alternatively, obliteration of the left atrial appendage could be accomplished with tapering or corkscrew occlusion device 154, as shown in FIG. 22. In tapering at both ends 68 and 70 device 154 approximates the conical or ellipsoid shape of the left atrial appendage of the heart.

Described herein is a covered self-expanding vascular plug 20, 20' for occluding blood vessels. The plug design evinces the ability to form both a tubular primary shape and an expanded spiraling or helical secondary shape of configuration 92, allowing for the occlusion of a wide range of vessel sizes from small to large via a microcatheter; this is not possible with current microcatheter deliverable plug designs. The largest diameter vessel that can be occluded via a microcatheter deliverable plug is currently 5 mm. The helical design described herein with its ability to create a large secondary shape, namely the spiraling or helical configuration 92 (also a property of the modified occlusion devices 120, 154, etc.) has the potential to occlude vessels of a much larger diameter than is currently possible with a microcatheter. As discussed hereinabove with reference to FIGS. 19A, 19B, 20A, 20B, one or more devices 20, 20', 154 could also be placed directly within the lumen of a saccular aneurysm 82 occluding its lumen while simultaneously sparing the parent vessel.

Vascular plug or occlusion device 20 is preferably covered with thin impervious membrane 23 except for the most down stream portion of the plug to allow blood to flow into or out of the device, enabling device repositioning or removal prior to deployment. In another version of the device 20 the plug body is not covered with an impervious membrane but is rather uncovered, covered with a porous membrane or coated with various thrombogenic materials such as small fibers or hydrogel to engender thrombosis by the three-dimensional spiraling superstructure or scaffolding after deployment. This latter design (uncovered, covered with a porous membrane, coated with fibers, or coated with hydrogel) might be of value in high flow situations to prevent initial device migration with vessel thrombosis occurring after a period of time. Changing the plug wall weave pattern to vary the plug porosity or a plug covering porous membrane could achieve a similar result.

One or more devices 20, 20', 120, 154 can be deployed as needed via the same microcatheter 18 to create stable interlocking subunits or constructs (FIGS. 12, 13A, 13B, 14A, 18C, 18D, 19B) in order to occlude large vessels or aneurysms 44, 77, 82. The spiraling or helical configuration 92 allows for the safe treatment of fusiform aneurysms 77 either by initial complete segmental occlusion across the entire aneurysm length with a single long device or by sequential occlusion, first reducing inflow to the fusiform aneurysm with a proximal plug 72, then crossing the first plug with the delivery catheter 74 via a patent channel or plug aperture 28, then occluding distally with one or more plugs 76, 78, followed by complete proximal occlusion after withdrawing the delivery catheter with placement of a final interlocking plug 80 (FIGS. 18A-18D).

The microcatheters typically used in clinical practice have internal luminal diameters of 0.021 inch or 0.027 inch. The use of a microcather allows navigation in tortuous vessels often not possible with larger 4 and 5 French outer diameter delivery catheters, typically having internal diameters of 0.040 inch and 0.046 inch respectively. However, the same helical plug design 20, 92 can be used to deliver even much larger occlusive devices through these larger lumen catheters. The unique large space filling capacity of the present spiraling tubular design can be used to occlude large arteries, veins, and aneurysms via a small microcatheter a distinct advantage over current methods. The ability to form a larger secondary shape from a primary subunit as is needed based on overall target vessel size is the key to the innovation. Multiple devices 20 can be deployed to form intertwined or interlocking structures or assemblies (FIGS. 12, 13A, 13B, 14A, 18C, 18D, 19B) that complete vessel closure and occlude an even larger vascular cross sectional area and volume. A modified device 154 with tapering ends 68 and 70 as shown in FIG. 15, FIGS. 20A, and 20B provide a mirror-symmetric corkscrew design that eliminates a patent central channel or passageway 28 extant in the spiraling or helical configuration 92 of the none-tapered versions of occlusion device 20. The modified tapering or corkscrew design 154 might also be ideal for placement in saccular aneurysms 82 or occluding the left atrial appendage 84, resulting in the creation of spheroid or ellipsoid shapes. The occlusion device 20 can be made in various lengths (compare, for instance, FIGS. 1A and 1B with FIGS. 7A, 7B, 8, 9) depending on the anticipated need for the secondary twisted or fully formed helical shape dictated by the target parent vessel size. The length and the diameter of primary subunit or tubular structure 22 may be varied to adapt the device to different indications. A minimum device length is dictated in part by the need to form the fully formed secondary shape to create one 360-degree turn, an important consideration for occluding larger vessels. Longer lengths might be used to treat long segment vascular pathology or fill large vascular spaces as might be seen in large aneurysms 77, 82.

While one or more second shaping wires might exemplarily extend in a spiral along an outer curve of the spiraling configuration 92, near a spiraling portion (not designated) of the outer wall 26 that engages a vascular endothelium on deployment of the device 20, it is understood that the outward forces generated by such shaping wires can be generated instead by manipulating the internal shape-memory forces of the wires or strands 17 of tubular structure 22. Moreover the large volume or cross sectional area of the secondary spiraling or helical configuration 92 of vascular plug or occlusion device 20 (or 20', 20", 120, 154, etc.) naturally militates against device migration. Endothelial tissues naturally become inserted in the continuous elongate gap or groove (not labeled) between adjacent turns or windings 19 of the device so that downstream movement of the device is resisted. This inserted endothelial tissue may become clamped or wedged between adjacent turns or windings 19, for instance, during compaction of a device 20 (or 20', 20", 120, 154, etc.), that is, during a change in conformation from that of FIG. 1A to that of FIG. 1B. This clamping or wedging contributes further to anchoring of the spiraling or helical configuration 92 at the selected deployment site in the target blood vessel. The physical size of device 20 (or 20', 20", 120, 154, etc.) limits the requirement for excessive radial force generation, as the device will become adhered to the endothelial wall of a blood vessel (44).

Although the invention has been described in terms of particular embodiments and applications, one of ordinary skill in the art, in light of this teaching, can generate additional embodiments and modifications without departing from the spirit of or exceeding the scope of the claimed invention. For instance, it will be understood by those skilled in the art of minimally invasive surgical procedures that the present plug or occlusion device 20 (or 20', 20", 120, 154, etc.) may be used to occlude pathologic nonvascular spaces related to the bowel, bile ducts, or ureters. Accordingly, it is to be understood that the drawings and descriptions herein are proffered by way of example to facilitate comprehension of the invention and should not be construed to limit the scope thereof.

What is claimed is:
1. A medical device comprising a superstructure expandable from a collapsed insertion configuration to a fully expanded deployment or use configuration,
said insertion configuration being sufficiently small to enable percutaneous introduction, said fully expanded deployment or use configuration being sufficiently large to extend across a target cavity in organic tissues of a patient and engage an inner surface of such cavity, said insertion configuration of said superstructure taking the form of a collapsed self-expanding tubular structure expandable to said fully expanded deployment or use configuration, said fully expanded deployment or use configuration being a three-dimensional twisted or helical form of said tubular structure, said twisted or helical form of said tubular structure having a plurality of turns or windings of respective outer diameters, said plurality of turns or windings including at least one terminal turn or winding at at least one of two opposite ends of said twisted or helical form of said tubular structure and further including at least one center turn or winding intermediate said two opposite ends, said at least one center turn or winding having an outer diameter that is larger than a largest outer diameter of said at least one terminal turn or winding, said fully expanded deployment or use configuration having an arcuate envelope or shape that tapers down at said at least one of said two opposite ends from said at least one center turn or winding.

2. The medical device defined in claim 1 wherein said superstructure includes an outer wall of said tubular structure and an inner wire made of shape memory material, said inner wire being operatively connected to said tubular structure to form said tubular structure into said twisted or helical form.

3. The medical device defined in claim 2 wherein said inner wire is connected to said tubular structure at one or more points along a length of said outer wall.

4. The medical device defined in claim 2 wherein said inner wire is a coiling shaping wire incorporated into or interwoven with said outer wall.

5. The medical device defined in claim 2 wherein said inner wire is a coiling shaping wire freely disposed in a lumen of said outer wall.

6. The medical device defined in claim 2 wherein said inner wire is a coiling shaping wire partially attached to a portion of said outer wall.

7. A kit or assembly comprising the medical device defined in claim 1 and further comprising an expandable plug configured for intertwining or interlocking with the medical device of claim 1, the medical device and the expandable plug being deployable in cooperation with one another for large vessel occlusion and catheter delivery.

8. The medical device defined in claim 1 wherein the outer diameter of said at least one center turn or winding of said fully expanded use or deployment configuration is sufficiently large to extend across and occlude largest vessels of a human cardiovascular system.

9. The medical device defined in claim 1 wherein said tubular structure is at least partially covered or enveloped by a membrane.

10. The medical device defined in claim 9 wherein said membrane is made of flow-impervious material.

11. The medical device defined in claim 9 wherein at least a downstream or trailing portion of said membrane is made of a porous material.

12. The medical device defined in claim 1 wherein said tubular structure is at least partially coated with a thrombogenic material, so that the device on implantation or deployment in a blood vessel results in a gradual vessel thrombosis, reducing chances of flow-related device migration.

13. The medical device defined in claim 12 wherein said thrombogenic material is taken from the group consisting of small fibers and hydrogel.

14. The medical device defined in claim 1 wherein said tubular structure has a cross section and associated outer diameter that taper down from said at least one center turn or winding towards said at least one of said two opposite ends.

15. The medical device defined in claim 14 wherein said cross section and associated outer diameter of said tubular structure taper down to terminal points at each of said opposite ends.

16. The medical device defined in claim 1 wherein said twisted or helical structure subtends a central channel, said central channel being closed off at least at said one of said two opposite ends owing to tapering down of the outer diameters of said turns or windings of said tubular structure along with simultaneous tapering or outer diameter reduction of said tubular structure at said at least one of said two opposite ends.

17. The medical device defined in claim 1 wherein said plurality of turns or windings includes at least one terminal turn or winding at each of said two opposite ends of said twisted or helical form of said tubular structure, said twisted or helical form of said tubular structure having an envelope or overall shape that is ellipsoidal or ovoid.

18. The medical device defined in claim 1 wherein said plurality of turns or windings includes at least one terminal turn or winding at each of said two opposite ends of said twisted or helical form of said tubular structure, said twisted or helical form of said tubular structure having an envelope or overall shape that is conical on one or both ends.

19. A medical method comprising:
providing two medical occlusion devices each having a superstructure with a fully expanded form that includes a tubular structure;
inserting, into a vascular system of a patient, a first one of said medical occlusion devices with the respective said superstructure in a collapsed configuration;
thereafter expanding the superstructure of said first one of said medical occlusion devices from the collapsed configuration to an adaptively expanded configuration inside a cavity in the patient so that the expanded superstructure of said first one of said medical occlusion devices extends across a selected portion of said cavity and engages an inner surface of said cavity, wherein the adaptively expanded configuration of said first one of said medical occlusion devices has an opening;
inserting, into the patient, a second one of said medical occlusion devices with the respective said superstructure in a collapsed configuration;
thereafter expanding the superstructure of said second one of said medical occlusion devices from the respective collapsed configuration to an expanded configuration inside a target blood vessel with an end portion of said second one of said medial occlusion devices inserted into said opening in the expanded superstructure of said first one of said medical occlusion devices so that the expanded superstructure of said second one of said medical occlusion devices occludes said opening in the expanded superstructure of said first one of said medical occlusion devices.

* * * * *